US012605539B2

(12) United States Patent
Adachi et al.

(10) Patent No.: US 12,605,539 B2
(45) Date of Patent: Apr. 21, 2026

(54) METHODS AND SYSTEMS FOR DELIVERING DRUGS THROUGH SKIN OF A BODY

(71) Applicant: PASSPORT TECHNOLOGIES, INC., San Diego, CA (US)

(72) Inventors: Hirotoshi Adachi, San Diego, CA (US); Uros Kascak, La Jolla, CA (US); Shohei Horie, San Diego, CA (US); Joe Hua, Rosemead, CA (US); Arjun Singh Bhungal, San Diego, CA (US)

(73) Assignee: PassPort Technologies, Inc., San Diego, CA (US)

( * ) Notice: Subject to any disclaimer, the term of this patent is extended or adjusted under 35 U.S.C. 154(b) by 968 days.

(21) Appl. No.: 17/623,155

(22) PCT Filed: Jun. 24, 2020

(86) PCT No.: PCT/US2020/039433
§ 371 (c)(1),
(2) Date: Dec. 27, 2021

(87) PCT Pub. No.: WO2020/264030
PCT Pub. Date: Dec. 30, 2020

(65) Prior Publication Data
US 2022/0257937 A1 Aug. 18, 2022

Related U.S. Application Data

(60) Provisional application No. 62/868,652, filed on Jun. 28, 2019.

(51) Int. Cl.
*A61N 1/28* (2006.01)
*A61K 9/70* (2006.01)

(52) U.S. Cl.
CPC .............. *A61N 1/28* (2013.01); *A61K 9/7084* (2013.01)

(58) Field of Classification Search
CPC .......... A61N 1/28; A61N 1/30; A61N 1/0412; A61N 1/0447; A61K 9/7038; A61K 9/7084; A61K 9/7092; A61M 2037/0007
See application file for complete search history.

(56) References Cited

U.S. PATENT DOCUMENTS

| | | | | |
|---|---|---|---|---|
| 5,885,211 A | * | 3/1999 | Eppstein | ........... A61M 37/0092 604/290 |
| 6,692,456 B1 | * | 2/2004 | Eppstein | ........... A61M 37/0015 607/2 |

(Continued)

FOREIGN PATENT DOCUMENTS

| | | |
|---|---|---|
| AU | 2014202524 A1 | 5/2014 |
| AU | 2016231468 A1 | 10/2016 |

(Continued)

OTHER PUBLICATIONS

International Search Report and Written Opinion issued in application No. PCT/US2020/039433, dated Oct. 13, 2020.

*Primary Examiner* — Emily L Schmidt
*Assistant Examiner* — Samuel J Marrison
(74) *Attorney, Agent, or Firm* — Knobbe Martens Olson & Bear LLP

(57) ABSTRACT

A transdermal permeant delivery system for delivery of at least one permeant into a tissue membrane of a subject comprises a filament array having a plurality of filaments that are disposed in a poration area and configured to deliver thermal energy to the tissue membrane to form a plurality of micropores; a applicator electrically connected to the filament array and configured to supply electrical energy to the filaments in order to create the plurality of micropores in the micropore area; and a patch configured for application on (Continued)

the micropore area and for releaseably containing at least one permeant. Method of treatment comprise using the transdermal permeant delivery system to administered a permeant in the form of a drug to a subject in need thereof.

27 Claims, 21 Drawing Sheets

(56) References Cited

U.S. PATENT DOCUMENTS

| | | | |
|---|---|---|---|
| 6,922,578 | B2 | 7/2005 | Eppstein et al. |
| 7,141,034 | B2 | 11/2006 | Eppstein et al. |
| 7,384,396 | B2 | 6/2008 | Samuels et al. |
| 7,758,561 | B2 | 7/2010 | Eppstein |
| 7,914,813 | B2 | 3/2011 | Adachi et al. |
| 8,517,958 | B2 | 8/2013 | Eppstein et al. |
| 8,641,689 | B2 | 2/2014 | Messier et al. |
| 8,706,210 | B2 | 4/2014 | Eppstein et al. |
| 9,486,616 | B2 | 11/2016 | Eppstein et al. |
| 9,498,609 | B2 | 11/2016 | Tagliaferri et al. |
| 9,579,380 | B2 | 2/2017 | Eppstein |
| 9,918,665 | B2 | 3/2018 | McRae et al. |
| 10,010,453 | B2 | 7/2018 | Harima et al. |
| 10,166,378 | B2 | 1/2019 | Tagliaferri et al. |
| 2005/0095578 | A1 | 5/2005 | Koller et al. |
| 2006/0034904 | A1* | 2/2006 | Weimann .......... A61M 37/0092 604/20 |
| 2007/0250018 | A1 | 10/2007 | Adachi et al. |
| 2011/0190688 | A1* | 8/2011 | Tagliaferri ............ A61M 37/00 604/20 |
| 2011/0264028 | A1* | 10/2011 | Ramdas ................ A61M 37/00 604/20 |
| 2015/0190074 | A1* | 7/2015 | McRae .................. A61B 5/685 600/309 |
| 2015/0342900 | A1 | 12/2015 | Putnins |
| 2019/0038884 | A1 | 2/2019 | Roux et al. |
| 2019/0070103 | A1 | 3/2019 | Ameri et al. |
| 2020/0023173 | A1 | 1/2020 | Smith et al. |

FOREIGN PATENT DOCUMENTS

| | | |
|---|---|---|
| CA | 2 676 255 A1 | 7/2008 |
| EP | 3 311 762 B1 | 7/2020 |
| EP | 3 411 110 B1 | 8/2020 |
| JP | 2012-219055 A | 11/2012 |
| WO | WO 2006/004595 A2 | 1/2006 |
| WO | WO 2008/091878 A1 | 7/2008 |

* cited by examiner

400 ⟍

402 ⟍

450 ⟍

600 —

640 —

680 —

1900

1920

2000

2020

METHODS AND SYSTEMS FOR DELIVERING DRUGS THROUGH SKIN OF A BODY

FIELD

Transdermal patches may be used to maintain a drug release and control a delivery of a drug or compound in a body. The transdermal patches typically comprise a reservoir containing an active permeant, such as a drug. The patch is generally attached to the body's skin and the drug or compound must, thus, pass through the skin. As such, a stratum corneum layer of the skin provides or acts as a barrier to the conveyance of the drug or compound into the body.

This disclosure relates to delivery of a drug or other compound via the skin. More specifically, this disclosure relates to enhancing the drug or compound delivery through skin to improve conveyance from the transdermal patches.

BACKGROUND

Transdermal patches deliver molecules of drugs or compounds from a reservoir such as a polymer matrix system into a body through the skin of the body. However, different layers of the skin may act as barriers to the delivery of the molecules, thereby creating a limitation on the drug delivery with respect to molecular weight (for example, molecule weights greater than 500 Da) of the molecules. The skin also introduces limitations on an optimal hydrophobic nature for such a passive transdermal drug delivery system.

Minimally invasive technologies and processes exist that improve capabilities of transdermal patches to convey larger molecular weights. For example, microneedles embedded in the transdermal patches and/or in the skin and/or micropores in the skin help to improve drug conveyance and/or increase the molecular weights of molecules that are conveyed between the transdermal patches and the body through the skin. Thus, such technologies improve delivery of large molecules and modify drug delivery profiles of the transdermal patches.

However, these technologies may still introduce limitations in the drug delivery from the transdermal patches to the body through the skin. For example, transdermal patches used in conjunction with the microneedle technologies may have limitations on the controlled delivery and/or drug loading amounts that are generally desirable features of transdermal patches. Thus, use of transdermal patches with the microporation technologies is generally preferable, as such a combination provides for more flexible drug delivery than with the microneedle technologies.

Thermal, radio frequency (RF), and laser microporation technologies exist. However, existing systems and methods do not utilize and/or generate micropores having optimal features and/or parameters for the drug being conveyed between the transdermal patches and the body via the skin. Instead, such systems may merely create micropores in the skin knowing that such micropores improve drug delivery but without being aware of and/or appreciating how to create optimal micropores for the delivery of drugs including large molecules. Thus, better systems and method for generating micropores that improve the delivery of drugs including large molecules are desired. In some embodiments, the micropores are created using microporation, thermal ablation, or flash vaporization, micro pathways in biological membranes or tissue (e.g., skin) can enhance the conveyance of the drug or compound into the body.

SUMMARY

Methods and apparatuses or devices disclosed herein each have several aspects, no single one of which is solely responsible for its desirable attributes. Without limiting the scope of this disclosure, for example, as expressed by the claims which follow, its more prominent features will now be discussed briefly. After considering this discussion, and particularly after reading the section entitled "Detailed Description" one will understand how the described features being described provide advantages that include data authentication services.

One innovation is transdermal permeant delivery system for delivery of at least one permeant into a tissue membrane of a subject. The transdermal permeant delivery system can include (a) a substrate having an upper substrate surface and defining a poration area, the substrate comprising a filament array having a plurality of filaments that are disposed in the poration area, wherein each filament is capable of conductively delivering thermal energy via direct contact to the tissue membrane to form a plurality of micropores in a micropore area of the tissue membrane that is in the range of 1% to 20% of the poration area, (b) an applicator electrically connected to the filament array and configured to supply a controlled amount of electrical energy to the filaments in order to create the plurality of micropores in the micropore area of the tissue membrane by heating the filaments, and (c) a patch configured for application on the micropore area and for releaseably containing at least one permeant, the patch comprising a matrix having a water-holding capacity that is less than 10 mg/cm$^2$ and at least one permeant dispersed in the matrix.

Various embodiments of the transdermal permeant delivery system disclosed here can include one, all, or any combination of features of this paragraph, or other features disclosed herein. The predetermined electrical energy to create the plurality of micropores by heating the filaments can be in the range of 0.0067 μJ/μm$^3$ to 0.0400 μJ/μm$^3$. The micropore area can be in the range of 1.25% to 10% of the poration area. The accumulated volume of the plurality of micropores can be in the range of 0.05 mm$^3$/cm$^2$ to 0.35 mm$^3$/cm$^2$. The permeant can be a long acting drug. The long acting drug can be a GLP-1 antagonist, a Fc protein, an antibody or a derivative thereof having an extended half-life. In some embodiments, the long acting drug acts for more than 24 hours. In some embodiments, the long acting drug can act for between 1 and 7 days. In some embodiments, the long acting drug acts for more than 7 days. The patch can be configured to release the permeant for more than 24 hours. The system can include a backing layer having at least a partial adhesive. The filament can include a conductive layer of copper and an underlying resistive layer of stainless steel. The applicator can be configured to supply the predetermined electrical energy to the filaments in the range of 2 mJ/filament to 12 mJ/filament, preferably in the range of 2 mJ/filament to 8 mJ/filament, more preferably in the range of 3 mJ/filament to 6 mJ/filament. The applicator can be configured to supply the predetermined electrical energy to the filaments for a time in the range of 2 ms to 16 ms, preferably in the range of 2 ms to 12 ms. The plurality of micropores in the micropore area are present at about 20 micropores/cm$^3$ to about 500 micropores/cm$^3$, preferably at about 50 micropores/cm$^2$ to about 400 micropores/cm$^2$. The accumulated depth of the plurality of micropores can be in the range of about 2500 $\mu$m/cm$^2$ to about 30,000 $\mu$m/cm$^2$. The matrix comprises at least one fiber. The matrix can include a laminated material, the laminated material comprising the fiber and a film. The fiber can have a thickness of less than 300 $\mu$m, preferably less than 200 $\mu$m. The areal weight of the fiber in the matrix can be less than about 100 g/m$^2$, preferably less than 20 g/m$^2$. The fiber can be a nonwoven fiber. The permeant can be dispersed in the matrix in an amount in the range of about 0.01 mg/cm$^2$ to about 20 mg/cm$^2$. In various embodiments, the permeant is a small molecule, a peptide, a protein, an oligonucleotide or a combination thereof.

Another innovation includes a transdermal permeant delivery system for delivery of at least one permeant into a tissue membrane of a subject, including a substrate having an upper substrate surface and defining a poration area, the substrate comprising a filament array having a plurality of filaments that are disposed in the poration area, wherein each filament is capable of conductively delivering thermal energy via direct contact to the tissue membrane to form a plurality of micropores in a micropore area of the tissue membrane, and an applicator electrically connected to the filament array and configured to supply a controlled electrical energy to the filaments in order to create the plurality of micropores in the micropore area of the tissue membrane by heating the filaments. The controlled electrical energy to create the plurality of micropores by heating the filaments is in the range of 0.0067 $\mu$J/$\mu$m$^3$ to 0.0400 $\mu$J/$\mu$m$^3$. In some implementations, the controlled electrical energy is a predetermined amount. In some embodiments, the controlled electrical energy is based at least in part on sensed information.

Another innovation includes a method of treating a subject in need thereof. The method can include identifying a subject having a condition in need of treatment by a selected drug, opening a plurality of micropores in the skin of the subject by applying the applicator of any of the transdermal permeant delivery systems disclosed herein to the subject, and applying the patch of the transdermal permeant delivery systems disclosed herein to the subject's skin over the micropore for a period of time, wherein the permeant dispersed in the matrix of the patch comprises the selected drug. The period of time can be selected to deliver a therapeutically effective amount of the selected drug through the plurality of micropores.

BRIEF DESCRIPTION OF THE DRAWINGS

These drawings and the associated description herein are provided to illustrate specific embodiments of the invention and are not intended to be limiting.

5 administered according to the parameters in Table 22 and a bar graph 2020 indicating Th1 cellular antibody titers in the body for groups 1-10.

Figure 21:
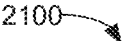
Figure 21:
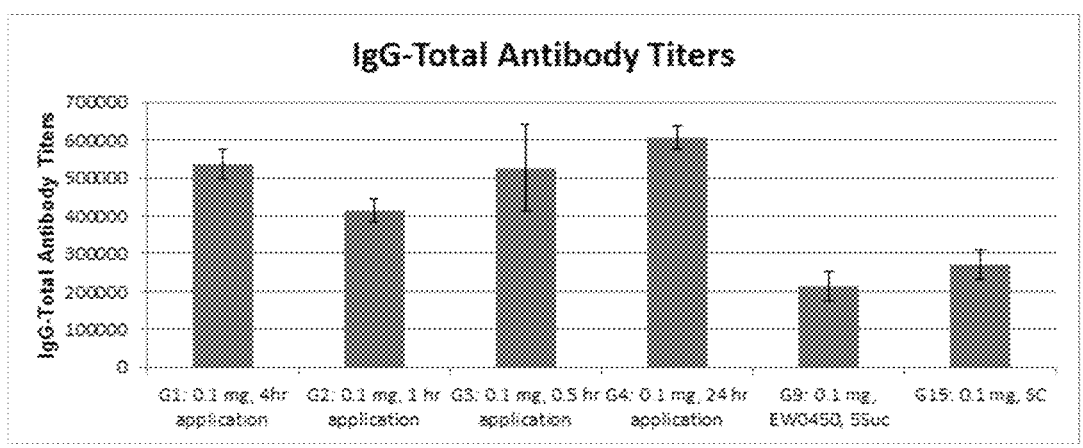
Figure 21:
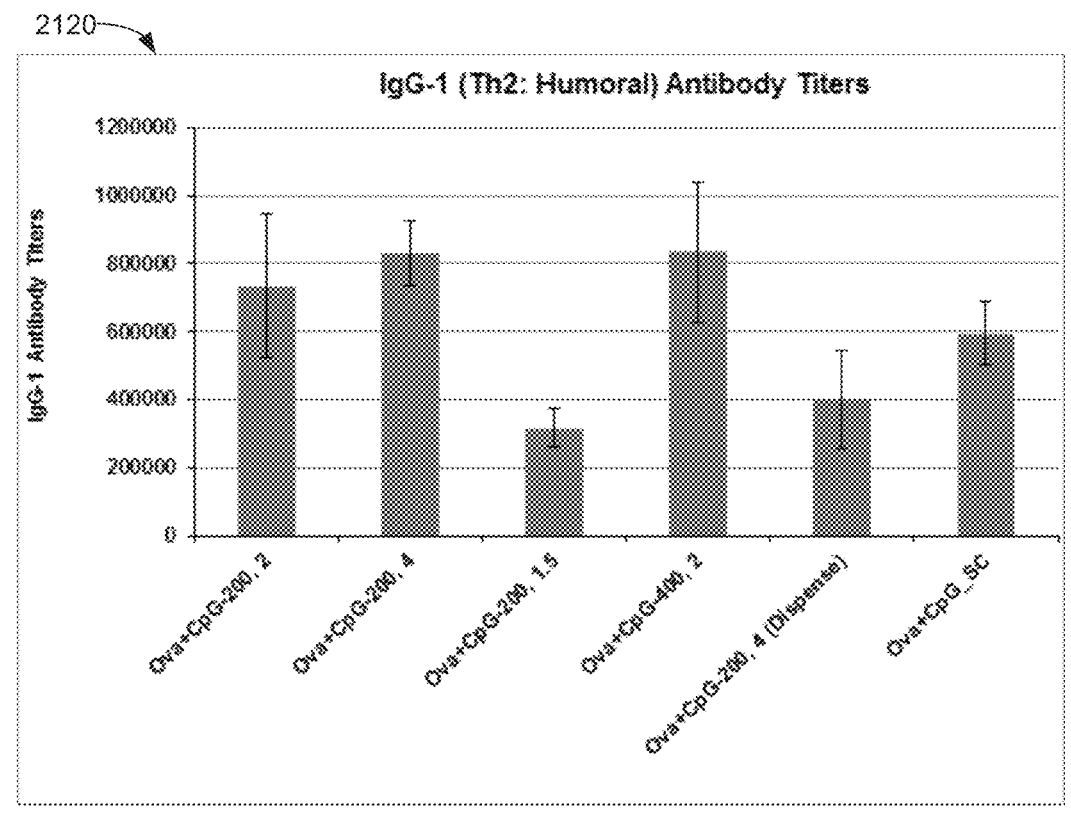

FIG. 21 shows a bar graph 2100 indicating a total amount of antibody titers in mice for groups 1-6 of vaccines administered according to the parameters in Table 22 and a bar graph 2120 indicating Th1 humoral antibody titers in the body for groups 1-6.

DETAILED DESCRIPTION

Although certain embodiments and examples are disclosed below, inventive subject matter extends beyond the specifically disclosed embodiments to other alternative embodiments and/or uses and to modifications and equivalents thereof. Thus, the scope of the application is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

In the following detailed description, reference is made to the accompanying drawings, which form a part of the present disclosure. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

The terminology used herein is for the purpose of describing particular implementations only and is not intended to be limiting on the disclosure. It will be understood that if a specific number of a claim element is intended, such intent will be explicitly recited in the claim, and in the absence of such recitation, no such intent is present. For example, as used herein, the singular forms "a," "an" and "the" are intended to include the plural forms as well, unless the context clearly indicates otherwise. As used herein, the term "and/or" includes any and all combinations of one or more of the associated listed items. It will be further understood that the terms "comprises," "comprising," "includes," and "including," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

High potency drugs (for example, long acting peptides, proteins, and oligonucleotides) are generally administered via injection delivery means. Other delivery methods may result in lower bioavailabilities of the drugs and/or a higher drug delivery (for example, rate, quantity, and so forth) variation than injections. Such variances may result in higher costs or reduced safety and/or effectiveness of the drugs.

Long acting drug formulations developed to minimize a frequency of injections and/or associated patient costs may have high and/or varying potencies. Thus, the long acting drug formulations are generally administered via injections, such as a depot formulation. Such injections may be more painful than typical injections because such injections may involve larger needles than general injections. Once an injection is done there is no way to remove the injected material if there is an adverse reaction (unlike a patch which may be removed). Injection site reactions can also occur. Such injections may have reduced compliance than injections with smaller sized needles. Thus, to improve patient compliance, needle-free and painless delivery and/or administration means for long acting drug formulations are desirable. The needle-free and painless delivery means should also be well-controlled to lower a risk of side effects.

Microporation (for example using laser, RF, and/or heating elements) may be controlled based on changing numbers of pores, pulse duration (quality of pores), and treatment area. However, variations in skin (for example, between different patients, between different locations on a patient's body, an environment of the patient, characteristics of the patient's skin, and so forth) may result in differences in micropore creation (regardless of the microporation method implemented) in different conditions or patients. Such differences may result in ineffective, inconsistent, unsafe, and/or variable drug delivery using transdermal patches in conjunction with known methods of microporation.

One embodiment of microporation utilizes thermal ablation to create the micropores. Though the examples provided in this disclosure may focus on microporation via such thermal ablation, the systems and methods described herein apply equally to other microporation methods and systems (for example, RF, laser, and so forth).

During poration of skin, the skin is ablated using metallic filaments brought to a high temperature by introducing electrical energy through the metallic filaments and into the skin. Fast introduction of the energy into the skin causes a rapid increase in a temperature of outer layers of the skin and results in ablation of at least a portion of the skin. The instant ablation ensures that the stratum corneum (the most outer protective layer of the skin which prevents ingress of foreign materials into a body protected by the skin and loss of bodily fluids) is removed from the skin. The removal of the stratum corneum provides an opening (i.e., a pore) having a depth that is proportional to the energy introduced through the metallic filaments and into the skin.

If the energy introduced through the metallic filaments is large enough and delivered quickly enough, ablating the stratum corneum exposes the epidermis (the layer of the skin which is aqueous and can be act as a conduit for a formulated active pharmaceutical ingredient). Introducing more energy into the skin will cause more of the epidermis (i.e., the water) to evaporate and result in deeper pores. The deeper pores will facilitate or provide a higher flux rate of the formulated active pharmaceutical, thereby providing a sufficiently desirable supply or concentration of the formulated active pharmaceutical via the skin.

The basic configurations of microporation drug delivery systems are known to those skilled in the art and thus do not require further elaboration herein. For example, transdermal permeant delivery systems are described in U.S. Pat. No. 8,116,860, which is hereby incorporated herein by reference and particularly for the purpose of describing various features of such microporation drug delivery systems. As described therein, the microporation drug delivery system of U.S. Pat. No. 8,116,860 (referred to therein using the reference number "10") comprises basic features that include a filament array (referred to therein using the reference number "70") configured to create the one or more pathways or micropores in a patient's skin and one or more transdermal patches (referred to therein using the reference number "100") containing at least one drug formulation. Other similar microporation drug delivery systems comprising such basic features are known to those skilled in the art. Various microporation drug delivery systems having such basic features are known to those skilled in the art and may be used or adapted for use by those skilled in the art guided by the teachings provided herein.

In some embodiments, the microporation device may be defined by a total area of pathways (for example, micropores) created in the skin by the one or more filaments and a total energy delivered to the one or more filaments to create the pathways. In some embodiments, the microporation device creates pathways such that the total area of pathways in the skin is between approximately 1-20% of a square centimeter (cm) of the skin. In some embodiments, the pathways in the skin may preferably comprise approximately 1.25-10% of the skin for each square centimeter of the skin exposed to the microporation device. In some embodiments, the ratio of 1.25-10%/cm$^2$ of skin provides effective drug delivery for drug formulations having a molecule size of or within a particular range. In some embodiments, the total energy delivered to the one or more filaments correlates to characteristics of the created pathways based on trans-epidermal water loss (TEWL) values of the skin.

In some embodiments, the energy delivered to the one or more filaments to create the pathways may be in the range of 0.0067 μJ/μm$^3$-0.0400 μJ/μm$^3$. The energy delivered to the one or more filaments may be delivered in pulses of between 2 and 12 milliseconds (ms) for sufficient energy to create consistent pathways to be delivered.

Characteristics of pathways that efficiently and safely deliver a drug through the skin, for example from a transdermal patch, may vary between in vitro and in vivo embodiments. For example, in some embodiments, the one or more filaments creates the pathway when energy of between 2 mJ/filament and 12 mJ/filament is applied to the one or more filaments for a pulse of between 2 and 16 ms. In some embodiments, the energy applied to the one or more filaments to create the pathway is between 2 mJ/filament and 8 mJ/filament or between 3 mJ/filament and 6 mJ/filament and the duration of the pulse is between 2 and 12 ms. In such embodiments, the one or more filaments may comprise or substantially be formed from stainless steel and having a volume (V) of 300,000 μm$^3$ (0.0067 μJ/μm$^3$-0.0400 mJ/μm$^3$) for 2 mJ/filament-12 mJ/filament. In some embodiments, the one or more filaments, arranged in a filament array, can create between 20 and 500 pathways/cm$^2$ of the biological membrane (e.g., skin) to which the one or more filaments are exposed. In some embodiments, the one or more filaments arranged in a filament array, can create between 50 and 400 pathways/cm$^2$ of the skin to which the one or more filaments are exposed.

In some embodiments, an accumulated (or summed) depth of all the pathways formed by the one or more filaments is between approximately 2500 and 30000 μm per square centimeter of skin exposed to the one or more filaments. In some embodiments, an accumulated or summed volume of all the pathways formed by the one or more filaments is between approximately 0.05 and 0.35 mm$^3$ per square centimeter of skin.

In some embodiments, the transdermal patch may have one or more characteristics that enhance the optimal drug release and diffusion of drug formulation into the body in conjunction with the pathways created by the microporation device. For example, the transdermal patch may comprise one or more of the following characteristics:

a polymer matrix comprising at least a fiber;
    a polymer matrix comprising a nonwoven fiber;
    a polymer matrix comprising a laminated material of film and fiber;
    a polymer matrix comprising a fiber having a thickness of less than 200 μm or 300 μm;
    a polymer matrix comprising a weight of fiber less than 20 g/m$^2$ or less than 100 g/m$^2$;
    a permeant comprising a weight of between approximately 0.01 and 20 mg/cm$^2$; and/or
    a permeant comprising a water-holding capacity of less than 20 mg/cm$^2$.

The improvements to the microporation device and the transdermal patch described herein enable the microporation drug delivery system to effectively and safely provide delivery of long acting drugs in a controlled manner. Embodiments of the microporation drug delivery system described herein may provide for improved patient compliance and enhanced drug delivery capabilities. Embodiments of the microporation drug delivery system may also provide for reduced risks of adverse effects caused by uncontrolled delivery and reduce development terms and costs for drugs for patients. Embodiments of the microporation drug delivery system also enables painless and needle-free self-administration of corresponding drugs by the patient a location of patient's choice, which leads to improved compliance and reduced costs (less visits to health care professionals). Embodiments of the microporation drug delivery system as described herein may be used for patients with a wide range of skin types, conditions, and so forth with a lower variation on individual drug delivery results. Embodiments of the microporation drug delivery system may work with a wide variety of drug formulations, for example high potency drugs, high molecular weight drugs, and biologics, among others. Embodiments of the microporation drug delivery system also enables delivery of the drugs with higher utilization (as compared to current transdermal patches) in an efficient and controlled manner, improving bioavailability of the drug in the patient's body.

Figure 1:
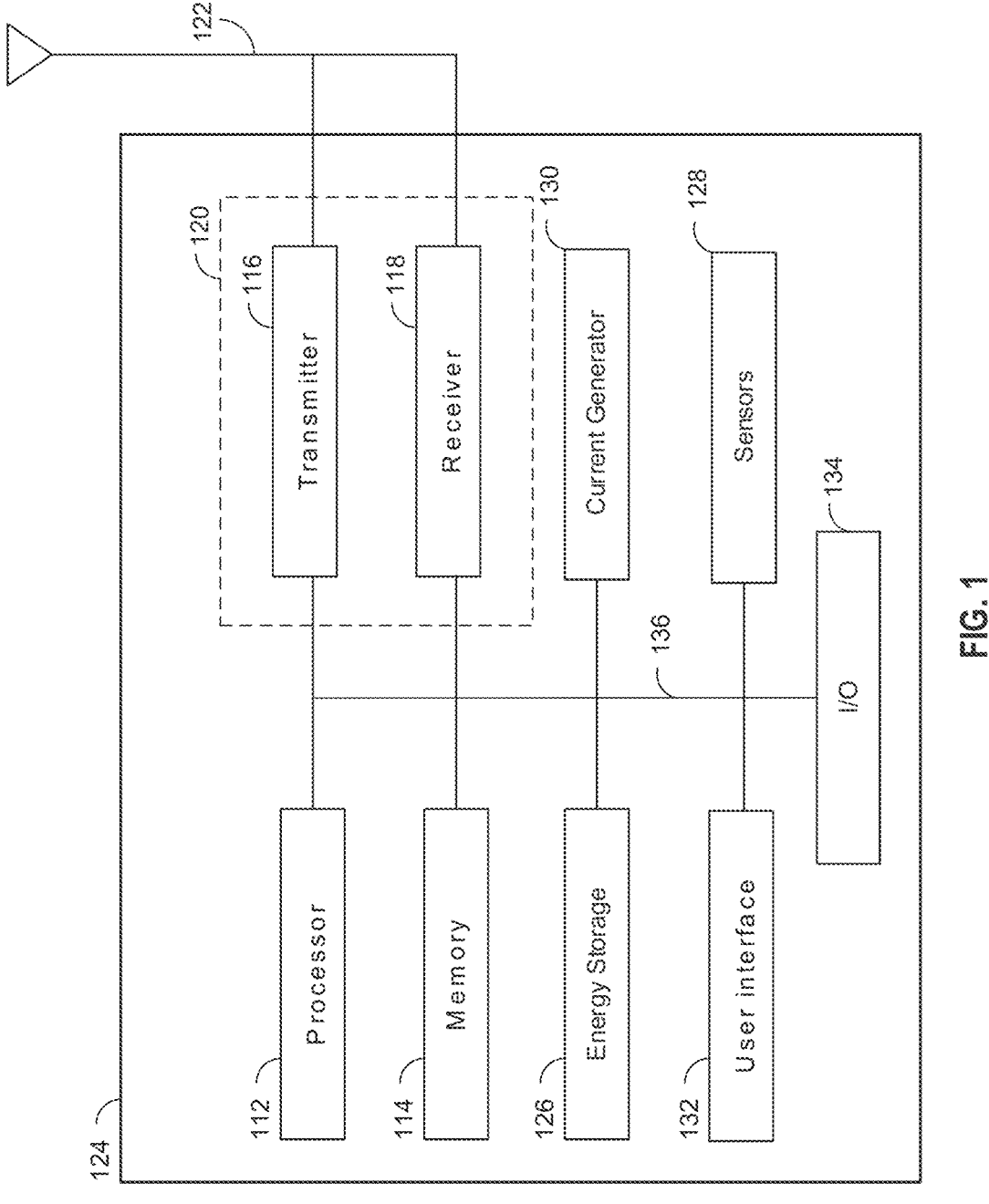
FIG. 1 is a functional block diagram of a control unit 110 of the microporation drug delivery system (for example, of the microporation drug delivery system 10 of U.S. Pat. No. 8,116,860).

FIG. 1 is a functional block diagram of a control unit 110 of the microporation drug delivery system (for example, of the microporation drug delivery system 10 of U.S. Pat. No. 8,116,860). The control unit 110 is an example of a hardware device or circuit that can implement the various methods described herein and provide the control and power to the one or more filaments of the microporation drug delivery system (for example, of the filament array 70 of U.S. Pat. No. 8,116,860). In some implementations, the control unit 110 does not include each of the components shown in FIG.

1. In some implementations, the control unit 110 includes additional components not shown in FIG. 1.

The control unit 110 includes a processor 112 which controls operation of the control unit 110. The processor 112 may also be referred to as a central processing unit (CPU) or hardware processor. The control unit further includes a memory unit 114, which may include both read-only memory (ROM) and random access memory (RAM), may provide instructions and/or data to the processor 112 and may serve as a repository for storage of instructions and/or data from the processor 112. A portion of the memory unit 114 may also include non-volatile random access memory (NVRAM). The processor 112 typically performs logical and arithmetic operations based on program instructions stored within the memory unit 114 or instructions and/or data received. The instructions in the memory unit 114 may be executable to implement the methods described herein. Furthermore, the control unit 110 may utilize the memory unit 114 to store information about other components in the microporation drug delivery system to enable the use of certain methods described below, for example, storing particular set points and/or operational characteristics for components in the microporation drug delivery system. The control unit 110 may then utilize the processor 112 in connection with the memory unit 114 to analyze the stored data and determine and/or identify various sets, categories, characteristics, or otherwise, for one or more of the other components in the microporation drug delivery system.

The processor 112 may comprise or be a component of a processing system implemented with one or more processors. The one or more processors may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

The processing system may also include non-transitory machine-readable media for storing software. Software shall be construed broadly to mean any type of instructions, whether referred to as software, firmware, middleware, microcode, hardware description language, or otherwise. Instructions may include code (for example, in source code format, binary code format, executable code format, or any other suitable format of code). The instructions, when executed by the one or more processors, cause the processing system to perform the various functions described herein. The processor 112 may further comprise a packet generator to generate packets for controlling operation and data communication.

The control unit 110 may include networking components, for example, a transmitter 116 and a receiver 118 to allow transmission and reception of data between the control unit 110 and a remote location or device. The transmitter 116 and the receiver 118 may be combined into a transceiver or network interface 120. The network interface 120 (and/or the transmitter 116 and the receiver 118) may communicate via a communication link 122, which may comprise a wireless or wired communication link. In some implementations, the communication link 122 may comprise a link to a mobile device or other user device used to monitor and/or track usage of the control unit 110 and/or the microporation drug delivery system. The network interface 120 operates with the processor 112 to communicate over the communication link 122.

The control unit 110 is covered by a housing unit or enclosure 124. The housing unit 124 may protect the components of the control unit 110 and/or the microporation device 101 from the environment and provide a packaging that is safe to handle and easy and convenient to use by a user.

The control unit 110 also includes one or more energy storage devices 126. The energy storage devices 126 may comprise a one or more batteries, capacitors, or similar energy storage components. The energy storage devices 126 provides energy to the components of the control unit 110 when the control unit 110 is in operation (for example, operating in the microporation drug delivery system).

In some implementations, the control unit 110 includes one or more circuits or sensors 128 configured to monitor an operation or a condition of one or more components of the control unit 110. For example, the sensors 128 may detect a state of charge and/or a state of health of the energy storage devices 126. Additionally, and/or alternatively, the sensors 128 may detect conditions of one or more components of the control unit 110 indicative of a malfunction of the control unit 110. For example, the sensors 128 may detect when one or more of the filaments has "blown" or is in an open circuit state or is deteriorating and approaching an open circuit state. Alternatively, or additionally, the sensors 128 may detect when too large or too small of a voltage or current is being conveyed to the filaments and/or when a temperature of the filaments is above, below, or at a desired threshold. In some implementations, the sensors 128 may be configured to monitor operation of the processor 112. Should the sensors 128 detect an overvoltage or over temperature condition or determine that the processor 112 is non-responsive, and then the sensors 128 may generate an output. In some implementations, the output from the sensors 128 may be communicated via the transmitter 116 or the network interface 120 over the communication link 122. In some implementations, the output from the sensors 128 may be communicated internally to another component of the control unit 110, for example the processor 112 or a user interface 132, described further below.

In some implementations, when the control unit 110 is initialized and/or when the microporation drug delivery system is activated, the sensors 128 perform an initial check to ensure all connections are proper and that all components of the microporation drug delivery system are in proper operating condition. Accordingly, the control unit 110 may perform an initial check of the microporation drug delivery system to determine if any malfunction exists. If no malfunction is detected in or by the control unit 110, then the control unit 110 begins providing a current to the filaments. If a malfunction is detected, then the control unit 110 may be prevented from providing a current to the filaments. Accordingly, the sensors 128 may function in or act as a safety circuit and prevent operation of the microporation drug delivery system in a malfunction state.

In some embodiments, the sensors 128 and/or the processor 112 may monitor a temperature of the conductive member. The processor 112 may further control the temperature of the conductive member to prevent filament failure, wherein the filament failure results in one or more filaments melting or failing into an open circuit state. In some embodiments, the temperature is determined based on the sensors 128 identifying a resistance of the conductive member and wherein controlling the temperature to prevent the filament failure comprises controlling the temperature to prevent the filament failure while the conductive member is in contact with at least one of the skin surface and air.

The control unit 110 also includes a current generator 130. The current generator 130 generates a current signal to be communicated via the filaments, as described herein. In some implementations, the current signal comprises one or more pulses. In some implementations, the pulses are varied to have one or more durations, amplitudes, etc., to control a temperature of the filaments and create pores in skin. In some implementations, the current signal may be a periodic pulse or a constant amplitude and frequency signal. For example, the current generator 130 may generate the current signal which is conveyed, via the control unit 110, to the filament array 104 with different properties during different periods of time. During a first period, or for a first duration of time, the current signal may be generated with a first set of attributes, for example as a single pulse or with a constant amplitude. During a second, subsequent period, the current signal may be generated with a second set of attributes, for example with a particular periodicity and particular amplitude.

In some implementations, based on the conditions detected using the sensors 128 or a command from the processor 112, the processor 112 allows or interrupts the generation and conveyance of the current signal to the filaments. In some implementations, interrupting the generation and conveyance of the current signal comprises terminating the current signal or reducing the current signal.

The control unit 110 further comprises a user interface 132, in some aspects. The user interface 132 may comprise a keypad and/or a display. The user interface 132 allows the user to control operation of the control unit 110 and/or the microporation drug delivery system. The user interface 132 may include any element or component that conveys information to the user of the control unit 110 and/or receives input from the user.

The control unit 110 further comprises an input/output (I/O) circuit component 134. In some implementations, the I/O circuit 134 may comprise a component that permits coupling of the control unit 110 to one or more other components in the microporation drug delivery system, such as the filaments. In some embodiments, the I/O circuit 134 includes a connector (for example, a universal serial bus (USB) connector, a proprietary connector, or any other connector) that physical connects the control unit 110 to the other component(s). In some implementations, the I/O circuit 134 comprises a component that detects an improper connection between the control unit 110 and/or the other component(s).

Various components of the control unit 110 may be coupled together by a bus system 136. The bus system 136 may include a data bus, for example, as well as a power bus, a control signal bus, and a status signal bus in addition to the data bus. Those of skill in the art will appreciate various components of the control unit 110 may be coupled together or accept or provide inputs to each other using some other mechanism.

Although a number of separate components are illustrated in FIG. 1B, those of skill in the art will recognize that one or more of these components may be implemented not only with respect to the functionality described above, but also to implement the functionality described above with respect to other components. For example, the processor 112 may be used to implement not only the functionality described above with respect to the processor 112, but also to implement the functionality described above with respect to the current generator 130 and/or the sensors 128. Each of the components illustrated in FIG. 1B may be implemented using a plurality of separate elements.

In some embodiments, one or more components of the control unit 110 may provide for locking of the control unit 110 such that the microporation drug delivery system cannot be abused or improperly used. Additionally, or alternatively, one or more components of the control unit 110 may count uses of or doses provided by the microporation drug delivery system and/or provide reminders regarding upcoming doses. In some embodiments, the network interface 120 may be used to communicate with a physician or pharmacy regarding refills of the formulated pharmaceutical as needed or to change the dosage, etc. In some embodiments, the user interface 132 may provide personalization of the microporation drug delivery system and provide voice prompts, guiding lights, etc., to simplify operation of the microporation drug delivery system.

In the microporation drug delivery system, the current signal generated by the current generator 130 of the control unit 110 and applied to the filament array 104 causes the filament array 104 to become heated and act as an energy/heat delivery medium. The filament array 104 provides sufficient amounts of energy/heat to the skin to ablate at least a surface (i.e., the stratum corneum) of the skin. In some embodiments, the amount of energy/heat conveyed to the skin by the filament array 104 is varied by varying the current that is delivered to the filament array 104 or by varying an amount of time that the filament array 104 conveys energy to the skin. For example, the current generator 130 may vary the amount of time that the filament array 104 conveys energy to the skin. In some embodiments, the amount of time may be varied by varying an amount of time that the filament array 104 is in contact with skin and/or by varying a pulse length of the current delivered to the filament array 104. For example, the current generator 130 may vary the pulse lengths of the current signal. In order to perform skin ablation, the current applied to the filament array 104 may cause the temperature of the filament array 104 to be above a melting point of the stratum corneum and the epidermis but below the melting point of the filament array 104. In various embodiments there can be a target temperature for the filament array 104. In some embodiments, a target temperature for ablation by the filament array 104 may be approximately 123° C. In other embodiments, a target temperature for ablation by the filament array 104 may be, for example within 1, 2, 3, 4, 5, 6, 7, 8, 9 or 10 degrees of 123° C. In some embodiments, a target temperature for ablation by the filament array 104 can be greater than 123° C.

Figure 2B:
FIG. 2B is a perspective view of the filament 200 of FIG. 2A, showing a cross-sectional area 208 and a current flow direction 210.
Figure 2B:
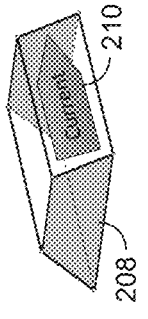
Figure 2A:
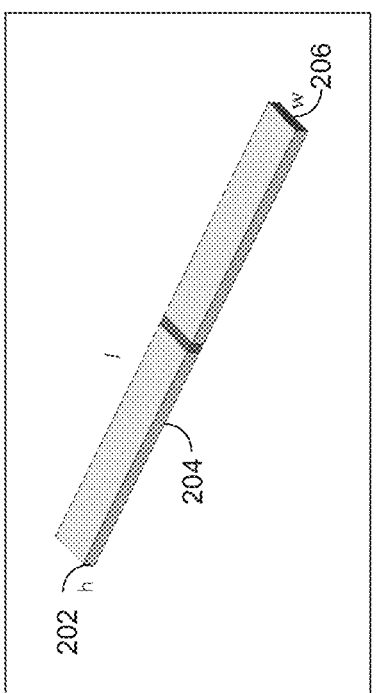
FIG. 2A is a perspective view of a filament 200 of the filament array 104 of the microporation drug delivery system.

FIG. 2A is a perspective view of a filament 200 of the filament array 104 of the microporation drug delivery system. As shown, the filament 200 has a three-dimensional shape with a height 202, a length 204, and a width 206. The filament 200 is formed from or comprises a conductive material (for example, stainless steel, aluminum, ferrite, or another a metallic or similarly resistive but not insulating material). In some embodiments, the filament 200 may be a microfilament or similar filament. For example, the filament 200 may be 50 μm wide, 15 μm thick, and 400 μm long. While the filament 200 shown has the shape of a generally rectangular block or prism, the filament 200 may have any other shape, such as a trapezoidal shape.

Various factors influence a balance of energy that is delivered to the filaments 200 and conveyed to the skin to create the pathways. For example, the filaments 200 of the filament array 104 may create the pathways in the skin by transferring sufficient energy from the filaments 200 to the skin to ablate the stratum corneum to expose the epidermis. The amount of energy transferred from the filament 200 to the skin may be based on a temperature difference between the skin and the filament 200, the material of the filament 200, properties of the skin (for example, skin type, morphology, elasticity, hydration, skin layers' thermodynamic parameters), and also contact/pressure between the filaments 200 and the skin. In some embodiments, a vacuum may be used to increase contact between the filaments 200 and the skin. For example, the filament array 104 may include holes or other structures that, when connected to a vacuum, cause the skin to be "sucked" toward the holes or structures, increasing contact between the filaments 200 and the skin. The amount of energy transferred may also be based on the electrical signal conveyed through the filament 200 (for example, one or both of the current, voltage, waveform, etc.). A distance between filaments of the filament array 104 may also impact the amount of energy transferred. The electrical parameters or factors identified may contribute to a supply of the energy/heat while the mechanical parameters may define sinking of the energy/heat. An electrical resistance of the filament 200 may depend, at least in part, on the material(s) used in the filament 200 and a shape of the filament and impacts the energy supplied by the filament 200.

In some embodiments, the control unit 110, for example via the sensors 128 and/or the processor 112, may determine whether a pressure applied to the skin surface by the conductive member (e.g., the filament array 104) is greater than or equal to a first pressure threshold.

FIG. 2B is a perspective view of the filament 200 of FIG. 2A, showing a cross-sectional area 208 and a current flow direction 210. As shown, the cross-sectional area 208 is a trapezoid and the current flows through the filament 200 in the current flow direction 210. However, the cross-sectional area 208 may be any shape (for example, a square, a rectangle, a circle, an ellipse, a triangle, another polygon, etc.) and the current flow may be in a direction substantially normal to the cross-sectional area 208 of the filament 200. Based on the current flowing through the filament 200 and the cross-sectional area 208, a current density/flux can be determined, according to Equation 1 below:

$$\text{Current Density}=I/A \qquad \text{(Equation 1)}$$

Where:
I—Current through the filament 200, and
A—cross-sectional area of the filament 200.

Based on Equation 1, as the cross-sectional area of the filament 200 increases, the corresponding current must be increased in order to maintain the current density. As the length of the filament 200 increases, the resistance of the filament 200 may increase, causing an increase in voltage and power for the increased mass of the filament 200.

The current density of the filament 200 may be used to identify an operational range of the filament array 104 that creates viable pores without inflicting pain or damaging the filament array 104, as will be described in further detail below. The depth of the pore created in the skin is proportional to the energy delivered to the skin via the filaments 200.

In some embodiments, the control unit 110 (for example, via the processor 112) determines a supply ratio of the current signal to the cross-sectional area of the filament 200. The control unit 110 further controls the supply ratio to be between a first threshold and a second threshold that is greater than the first threshold.

Figure 3B:
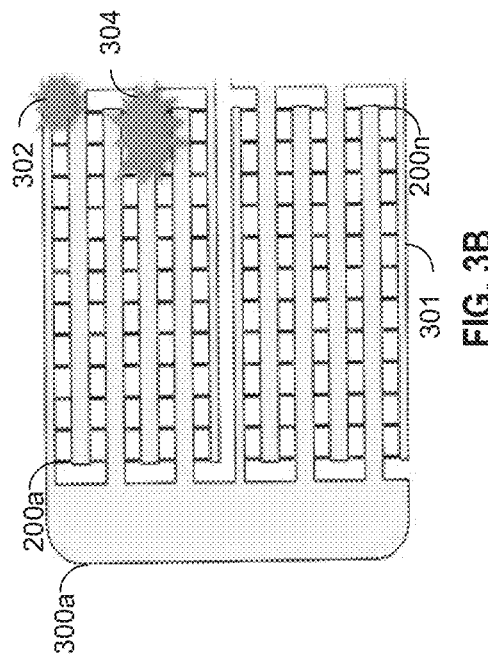
FIG. 3B is a top view of the filament array 104 of FIG. 3A experiencing one or more filament failures 302 and 304.
Figure 3A:
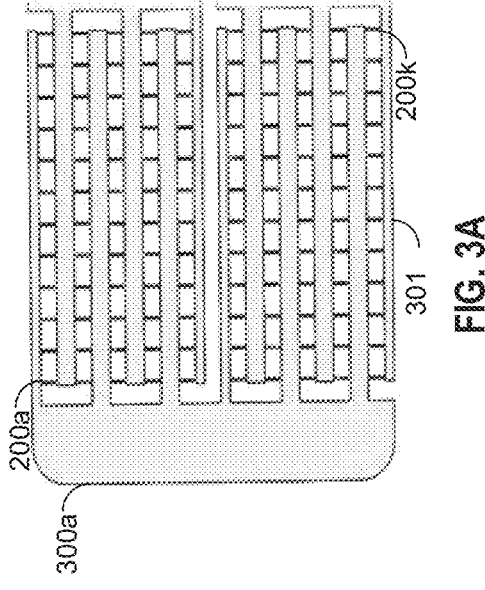
FIG. 3A is a top view of a representative filament array 104 of the microporation drug delivery system comprising a plurality of the filaments 200 of FIGS. 2A and 2B.

FIG. 3A is a top view of a representative filament array 104 of the microporation drug delivery system comprising a plurality of the filaments 200 of FIGS. 2A and 2B. The filament array 104 includes the plurality of filaments 200 disposed between conductive supporting members or structures 300. Though not shown in FIG. 3A, the conductive supporting member 300 may be coupled to a power source.

In some embodiments, the conductive supporting members 300 are made of copper or a similar conductive material. In some embodiments, the conductive supporting members 300 are a different material from the filaments 200. As shown in FIG. 3B, the conductive supporting member 300a includes fingers or similar projections 301 between which the filaments 200a-200k are disposed, where 1<k. Though not shown, a corresponding conductive supporting member may exist with fingers 301 interleaved with the fingers 301 of the conductive supporting member 300a.

The conductive supporting members 300 provide structural support to the filaments 200 by holding the filaments 200 in place between the fingers of the conductive supporting members 300. Additionally, and/or alternatively, the conductive supporting members 300 conductively couple the filaments 200 to the power source.

In some embodiments, using one or more components of the microporation drug delivery system to control or vary an amount of time that the filaments 200 convey energy to the skin may be simpler and more efficient than controlling the current conveyed via the filaments 200. For example, such control of the amount of time may utilize fewer components than a system that controls or varies the current delivered to the filaments 200. However, when controlling or varying the amount of time that the filaments 200 convey the energy to the skin, the control unit 110 may prevent a slow rise in the temperature of the skin that can "cook" and/or damage or dry the top layers of the skin (for example, the stratum corneum and/or the epidermis). Such cooking and/or drying out of the top layer(s) of the skin may create a charcoaled/dried layer of dead tissue of the skin. This layer of dead tissue may obstruct heat distribution from the filaments 200 into deeper layers of the skin (for example, the epidermis) and prevent the creation of viable pores for delivery of the formulated active pharmaceutical. Additionally, the cooking and/or drying out of the top layer(s) of the skin (i.e., exposure of the skin to the heat) may trigger a nerve reaction in the skin that causes or is interpreted as pain. Accordingly, the duration of the heat pulse or the duration of time during which the filaments 200 are in contact with the skin is less than a time that will cook or dry the top layers of skin.

Additionally, increasing the current through the filaments allows the filaments to reach a target temperature (i.e., heat up very quickly) in a shorter period of time as compared to a relatively lower current through the filaments. Additionally, the increased current shortens the time needed to create desired pore size, thus reducing or eliminating the risk of the nerve reaction to the heat and reducing or eliminating pain associated with the ablation.

When the current generator 130 and the control unit 110 supply a large current to the filament array 104, the individual filaments 200 in the filament structure 104 experience a rapid increase in temperature. The increase in temperature of the filaments 200 (and, correspondingly, the filament array 104) may shorten a time needed to create target pore size. Thus, the risk of the nerve reaction to the heat due to cooking and/or drying is reduced or eliminated and the pain associated with the ablation may be reduced or eliminated.

As described above, the filaments 200 in the filament array 104 convey the energy/heat from the power source (e.g., the control unit 110 of FIG. 1) coupled to the conductive supporting members 300 to the skin. Each filament 200 has one or more properties that may impact the energy/heat conveyance to the skin. For example, the filament 200 has an electrical resistance that depends on the material used for the filament and the mechanical shape of the filament. An amount of energy supplied to and by the filament is based on a current applied to the filament 200 (i.e., based on the current generated by the current generator 130), the electrical resistance of the filament 200, and the size of the filament. The energy supplied to the filament can be calculated using Equations 2 and 3 below:

$$E=P*t=I*U*t=I^2*R_f*t=U^2/R_f*t \qquad \text{(Equation 2)}$$

$$R_f=\rho*l/(w*h) \qquad \text{(Equation 3)}$$

Where:

E—energy.

P—power, t—time,

I—current flowing through the filament 200,

U—voltage on the end of the filament 200,

Rr—resistance of the filament 200, $\rho$—specific material resistivity of the filament 200, l—length of the filament 200, w—width of the filament 200, and h—height (thickness) of the filament 200.

An amount of energy supplied to and by the filament array 104 is based on a current applied to the filament array 104 (i.e., based on the current generated by the current generator 130) and the overall resistance of the filament array 104. The overall resistance of the filament array 104 is determined by averaging the filaments 200 of the filament array 104. The energy supplied to and by the filament array 104 can be calculated using Equations 4 and 5 below:

$$E=P*t=I*U*t=I^2*R_a*t=U^2/R_a*t \qquad \text{(Equation 4)}$$

$$R_a=R_f/N_{fb}*N_b) \qquad \text{(Equation 5)}$$

Where:

E—energy,

P—power, t—time,

I—current flowing through the filament array 104,

U—voltage on filament array 104 contacts, and $R_a$—average resistance of the filament array 104 (depends on the bank configuration and the array configuration).

FIG. 3B is a top view of the filament array 104 of FIG. 3A experiencing one or more filament failures 302 and 304. A filament failure occurs when one or more of the filaments 200 of the filament array 104 are damaged and/or destroyed such that the damaged or destroyed filament 200 is unable to conduct the generated current from the current generator 130 to the skin. For example, if one of the filaments 200 is cut, broken, or melted such that the filament 200 does not connect two fingers 301 of the conductive supporting members 300, then that filament 200 is broken, blown, or otherwise failed. Accordingly, when in a failed state, the filament 200 effectively acts as an open circuit between the fingers 301 of the conductive supporting members 300. The filament failures 302 and 304 correspond to individual failed filaments 200 that no longer provide a conductive path between the respective fingers 301 of the conductive supporting members 300 to which the failed filaments 200 are coupled.

In some embodiments, the failure of one of the filaments 200 in the filament bank between two fingers 301 may cause a cascading filament failure. For example, when a first filament 200a in the filament bank 1 fails, the remaining filaments 200 in the filament bank 1 experience an increase in power flow due to the lost path through the failed filament 200a. This increased power flow through the remaining filaments 200 in the filament bank 1 increases a risk of one or more of the remaining filaments 200 failing as well. While the failure of just the filament 200a may not initiate the cascading (avalanche) effect in the remaining filaments 200 of the filament bank 1, if a sufficient number of filaments 200 in the bank 1 fail (for example, about 5% of the filaments 200 in the bank 1), the cascading filament failure may occur. Accordingly, eventually all the filaments 200 in the bank 1 will fail, causing a complete cascade failure, or open failure. An amount of time that passes between the initial filament failures and the resulting complete cascade failure depends of the amount of current/energy supplied to the filaments 200 that is not dissipated into one of three manners, described below.

In some embodiments, the filaments 200 are cooled, by which the energy supplied to the filament 200 is dissipated. Three ways in which such dissipation occurs include: (1) radiation of heat into air, (2) conduction of the heat into the filament array 104 (for example, the copper structure), and (3) conduction of the heat into the skin. Radiation of the heat from the filament 200 into the air is a relatively small drain of heat as compared to the heat conduction into the filament array 104 or into the skin. Accordingly, the radiation heat loss may generally be ignored.

The conduction of the heat (back) into the conductive supporting structure 300 (for example, made of copper) is relatively large because the conductive supporting structure 300 is substantially metal, which generally conducts heat. An amount of heat loss due to conduction into the conductive supporting structure 300 can be quantified using thermal laws of physics and known material properties, and will not be described in detail herein.

As noted above, the conduction of heat to the skin depends on various properties of the skin, including at least one or more of skin type, morphology, elasticity, hydration, and thermodynamic parameters of skin layers, and also contact/pressure between the filament array 104 and the skin. The relevant properties of the skin may change during poration, as different layers of skin have different properties that affect the heat conduction. For example, as the dry stratum corneum (having a laminar structure that has varying consistency and thickness between different entities with skin) is ablated with the filament array 104, the epidermis is exposed, which is generally more hydrated and has different properties than the dry stratum corneum.

As previously described, the electrical resistance (and thus temperature) of the filament 200 is proportionate to the size and/or shape of the filament 200 and the energy (i.e., the generated current from the current generator 130) delivered to the filament 200. To accommodate various sizes, shapes, and energies, the relationships can be normalized using the current density defined by Equation 1 above. Based on the current densities defined by Equation 1, the operating constraints that result in failure of the filaments 200, and operating constraints that result in ablation of the stratum corneum, a range of desirable current densities is defined. The defined range of current densities identifies those current densities that, if delivered to the filaments 200, create viable pores without inflicting pain or damaging the filament array.

A total energy provided to the filament 200 during a period of time is defined by Equation 6:

$$E=E_{Wu}+E_M \qquad \text{(Equation 6)}$$

Where:

$E_{WU}$ is energy conveyed in warmup pulses (for example, pulses that bring the temperature of the filament 200 up to a desired or operating temperature with desired or operating dynamics);

$E_M$ is energy conveyed in maintenance pulses (for example, pulses that maintain the filament 200 at a substantially constant temperature level (for example, the desired or operating temperatures), thus balancing out any heat losses experienced by the filament 200).

$E_{WU}$ may be proportional to:

$\rho$—a specific resistance of the material(s) of the filament 200 (temperature dependent);

T—an operating or desired temperature that the filament 200 should reach in operation;

$i_Q$—a current flux/density (mA/$\mu m^2$)-squared (E=$I^2$*R*t);

l—a length of the filament 200;

m or V—a mass or volume of the filament 200 that needs to be heated up; and t—a time value or period (for example, a WU pulse duration).

$E_M$ may comprise a sum of the heat losses is defined by Equation 7:

$$E_M = E_S + E_{CT} + E_R + E_{CV} \qquad \text{(Equation 7)}$$

Where:

$E_S$ is energy (for example, heat) lost (conducted) into the skin (substrate);

$E_{CT}$ is energy lost into the traces (conductive structure) of the filament array 104;

$E_R$ is energy lost or radiated;

$E_{CV}$ is energy lost by convection.

Because the $E_R$ and $E_{CV}$ values are negligible or generally zero, EH need only generally compensate for $E_{CT}$ and $E_S$ losses, which may be the losses due to resistance of the filament 200 and/or energy conveyed to the skin to create the pathways (for example, distributed between losses in the traces of the filament 200 and evaporating water (living tissue) of the skin). The $E_S$ may be proportional to:

$\Delta T$—a temperature difference between the filament 200 and the skin (substrate);

h—a coefficient of a heat transfer between the filament 200 and the skin;

$A_S$—a surface area of contact between the filament 200 and the skin; and t—a time corresponding to how long the maintenance pulse is "On" or active Thus, since $E_M$ maintains the temperature of the filament 200 at a substantially constant level, the energy conveyed to the filament 200 during the maintenance period is directly proportional to the amount of water evaporated from the skin. Accordingly. $E_M$ can be determined based on Equation 8, which governs water evaporation from skin:

$$E_M = i_2 * R_T * t = (h * A_S * \Delta T * t) + E_{CT} \qquad \text{(Equation 8)}$$

Where:

i is current per filament 200; and $R_T$ is resistance of the filament 200 at an equilibrium temperature.

Since both $E_M$ and $E_{CT}$ are time dependent, Equation 8 can be reduced and expressed as a power delivered to the filament 200 as shown in Equations 9-11:

$$E_M = i^2 * R_T = (h * A_S * \Delta T) + P_{CT} \qquad \text{(Equation 9)}$$

$$E_M = (i_Q * A)^{2} * (\rho_T * l/A) = (h * A_S * \Delta T) + P_{CT} \qquad \text{(Equation 10)}$$

$$E_M = i_Q^{2} * A * \rho_T * l = (h * A_S * \Delta T) + P_{CT} \qquad \text{(Equation 11)}$$

Where:

$\rho_T$ is a specific resistance of the filament 200 at the operating temperature;

A is an average cross-sectional area of the filament 200; and h is a heat transfer constant between two materials (for example, the filament 200 and the skin).

The combination of variables (h*$A_S$*$\Delta T$) corresponds to the energy conveyed to the filaments 200 to evaporate water from the skin. Since h and $\Delta T$ may be relatively constant for a particular combination of filaments 200 and skin, the cross-sectional area of the filaments 200 ($A_S$) may be highly determinative of the amount of water evaporated from the skin and/or the volume of the pathways generated. Furthermore, as the volume of the filaments 200 increases, the energy delivered via the filaments 200 and transferred to the skin is increased. However, in some embodiments, the volume of the filaments 200 can be increased by increasing length of the filaments 200 as opposed its cross-section to stay within the range of functional current densities achievable via the microporation drug delivery system. Additionally, increased cross-sections of the filaments 200 may increase losses in the $P_{CT}$ that do not contribute to the pore size of the pathways. In some embodiments, more complex and larger cross-section areas of the filaments 200 can increase energy transfer to the skin while reducing or keeping energy losses small. For example, using the filaments 200 of FIGS. 3A and 3B, the A=w*d (width times thickness), $A_S$=w*l (touching the skin only at a bottom surface of the filaments 200), and $P_{CT}$ is proportional to the A. Thus, the Equation 11 simplifies to Equation 12 below:

$$E_M = i_Q^{2} * w * d * \rho_T * l = (h * w * l * \Delta T) + (const * w * d * \Delta T) \qquad \text{(Equation 12)}$$

In some embodiments, a heat transfer from the filament 200 to the skin is not dependent on the thickness of the filament 200 and the energy delivered to the skin (and the resulting volume of the pathways) will be bigger as a length of the filament 200. For example, based on the current density of $i_Q$=2.67 mA/$\mu m^2$, with 400 filaments 200 having a length of 400 microns, width of 50 microns, and thickness of 15 microns, approximately 3 mJ per filament 200 are used to create minimum viable pathways. In some embodiments, viable pathways are formed using filaments 200 with applied energies of between 2 mJ/filament and 12 mJ/filament, between 2 mJ/filament and 8 mJ/filament, or between 3 mJ/filament and 6 mJ/filament (as demonstrated by TEWL studies). Such filaments 200 may be formed from stainless steel and have a value of 30000 $\mu m^3$, thereby resulting in between 0.0067 $\mu J/\mu m^3$ and 0.0400 mJ/$\mu m^3$ for 2 mJ/filament-12 mJ/filament. In some embodiments, the relationship between the applied energy to the filaments 200 and the TEWL is linear. Furthermore, comparing different sizes of filaments 200 with same sized volumes of the filaments 200 suggests that the drug delivery of the filaments 200 stays the same while the volume of the filaments 200 is the same. Based on the analysis herein, an ideal energy for heating the filaments 200 in the microporation device 101 to create the pathways may be between 0.0067 $\mu J/\mu m^3$ and 0.0400 $\mu J/\mu m^3$, where V is the volume of the filaments 200.

For example, the filament array 300a comprises 200 filaments with filament lengths of 500 microns ($\mu m$), filament widths of 50 $\mu m$, filament thicknesses of 15 $\mu m$, and $i_Q$ values of 2.67 mA/$\mu m^2$ and the time it would take for this filament array 300a to reach the desired or operating temperature is about 700-800 ms and uses about 2 mJ of energy per filament 200 to reach the desired or operating temperature.

Alternatively, or additionally, when the filament array 300a comprises 400 filaments with filament lengths of 400 microns (μm), filament widths of 50 μm, filament thicknesses of 15 μm, and $i_O$ values of 2.67 mA/μm$^2$, the time it would take for this filament array 300a to reach the desired or operating temperature is about 700-800 ms and about 1.5 mJ of energy would be used per filament 200 to reach the desired or operating temperature.

Figure 4:
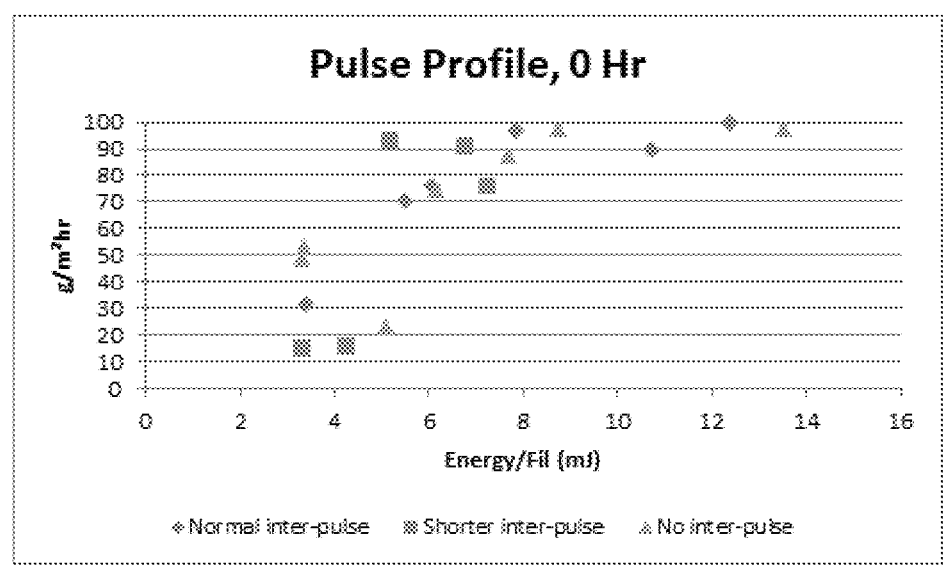
FIG. 4 is a graph 400 showing a pulse profile showing a relationship of TEWL to energy delivered via pulses to the filament array of the microporation drug delivery system and graph 450 showing a relationship of energy delivered versus the TEWL for a high powered applicator (HPA) that created approximately 400 pathways.
Figure 4:
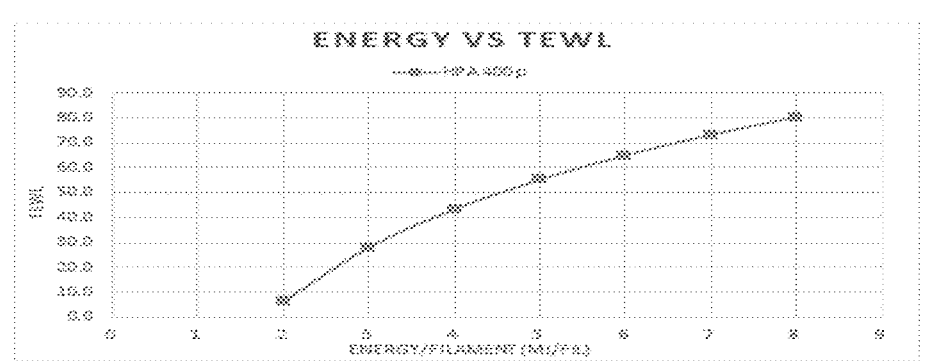

FIG. 4 is a graph 400 showing a pulse profile showing a relationship of TEWL to energy delivered via pulses to the filament array of the microporation drug delivery system and graph 450 showing a relationship of energy delivered versus the TEWL for a high powered applicator (HPA) that creates approximately 400 pathways. In various embodiments, a HPA can create more pathways, and it can depend at least in part the size of the filaments. For example, with certain parameters it can create up to about 1,600 pathways. Utilizing state of the art manufacturing techniques, it can be about 2,000 pathways. If the design and/or the geometry of filaments (and/or materials) are changed, the number of pathways can be higher.

The graph 400 shows that with an average filament 200 volume of 300,000 μm$^3$, using the filaments 200 formed from stainless steel having a width of 50 μm, length of 400 μm, and depth of 15 μm, about 400 pathways are formed in the skin in 10% of the area of the skin to which the filaments 200 are exposed. The graph 400 shows that for different levels of inter-pulse (normal inter-pulse, shorter inter-pulse, no inter-pulse) different energies result in different TEWL. For example, for normal inter-pulses of about 6 mJ/filament, the TEWL is about 75 g/m$^2$ hr. For shorter inter-pulses of about 7 mJ/filament, the TEWL is about 75 g/m$^2$ hr, and for no inter-pulses of about 6 mJ/filament, the TEWL is about 73 g/m$^2$hr.

The graph 450 shows the general relationship between the TEWL as a function of energy applied to the filaments 200. The range of energy applied to the filaments, as described above, is 2 mJ/filament to 12 mJ/filament. The line 452 shows that as the energy/filament increases (for energy levels above 2 mJ/filament), the resulting TEWL increases, though at increasingly smaller or reduced rates. For example, the ΔTEWL between 2 mJ/filament and 3 mJ/filament is larger than the ΔTEWL between 5 mJ/filament and 6 mJ/filament. Thus, the graph 450 shows that TEWL appears to generally saturate as the energy/filament increases, such that energies of greater than 12 mJ/filament may provide minimal TEWL increases. Furthermore, higher energies/filament may not be desired to avoid pain and/or discomfort in the patient. Therefore, the graphs 400 and 450 indicate that energies applied to the filaments may be maintained between 3 mJ/filament and 10 mJ/filament to maximize TEWL while maintaining patient comfort and not wasting energy.

Figure 5:
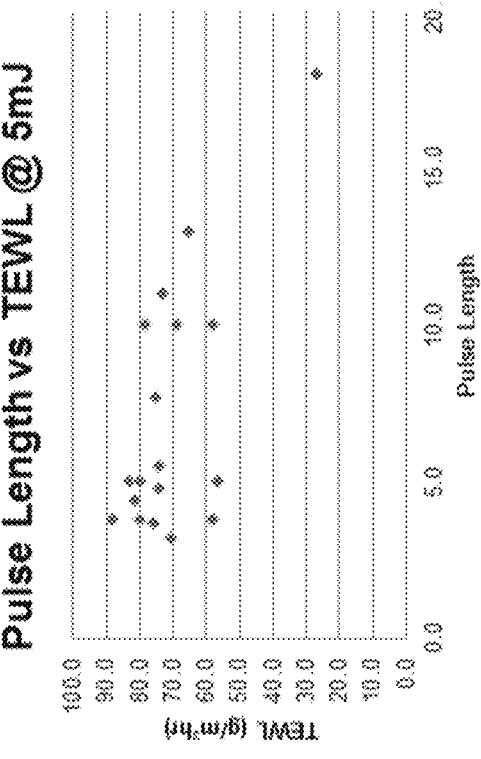
FIG. 5 is a graph 500 showing a pulse TEWL as a function of pulse length with a given energy per filament.

FIG. 5 is a graph 500 showing a pulse TEWL as a function of pulse length with a given energy per filament. The graph 500 includes pulse length (time) along the x-axis and TEWL along the y-axis. The various dots or markers show what pulse lengths result in what TEWL.

The graph 500 shows that with an average filament 200 volume of 300,000 μm$^3$, using the filaments 200 formed from stainless steel having a width of 50 μm, length of 400 μm, and depth of 15 μm, about 400 pathways are formed in the skin in 10% of the area of the skin to which the filaments 200 are exposed when approximately 5 mJ/filament of energy is applied. The graph 500 shows that for different lengths of pulses between approximately 3 ms and 18 ms, different levels of TEWL are obtained. The 500 also shows that TEWL does not begin to decay noticeably until pulse lengths exceed 12 ms and that, thus, energy delivery is long pulses is inefficient. Thus, as described above, pulse lengths for the microporation device 101 may be maintained at less than 12 ms.

Figure 6:
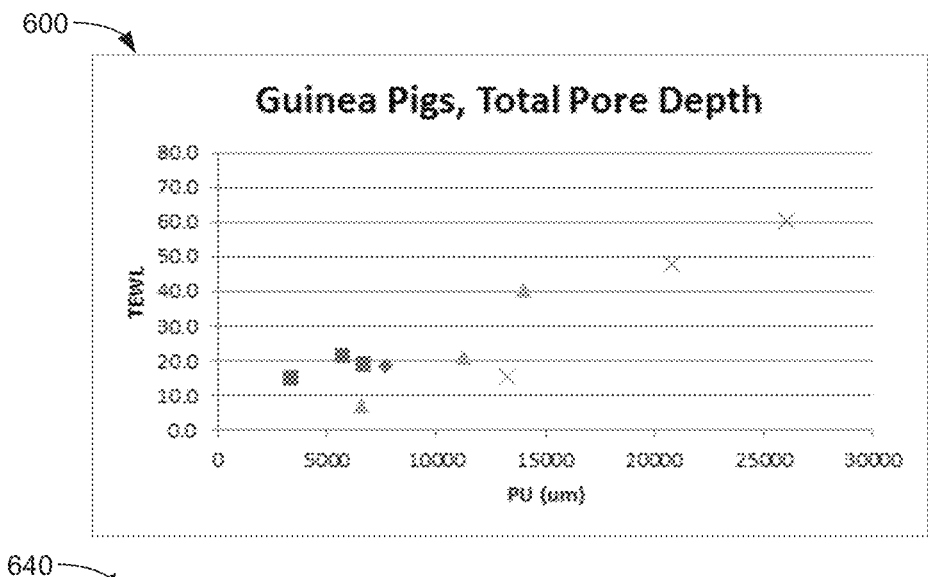
FIG. 6 is a graph 600 showing TEWL as a function of total pathway depth, a graph 640 showing TEWL as a function of total pathway area, and a graph 680 showing TEWL as a function of total pathway volume.
Figure 6:
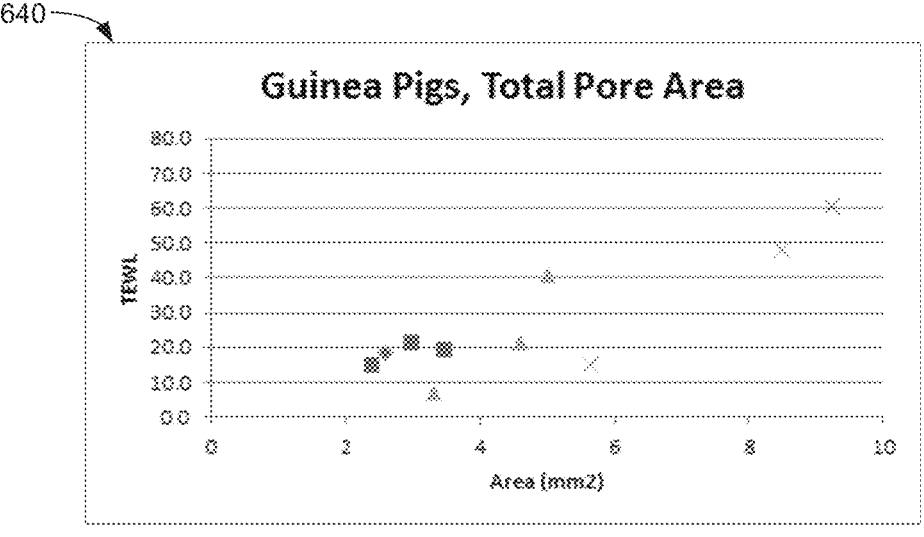
Figure 6:
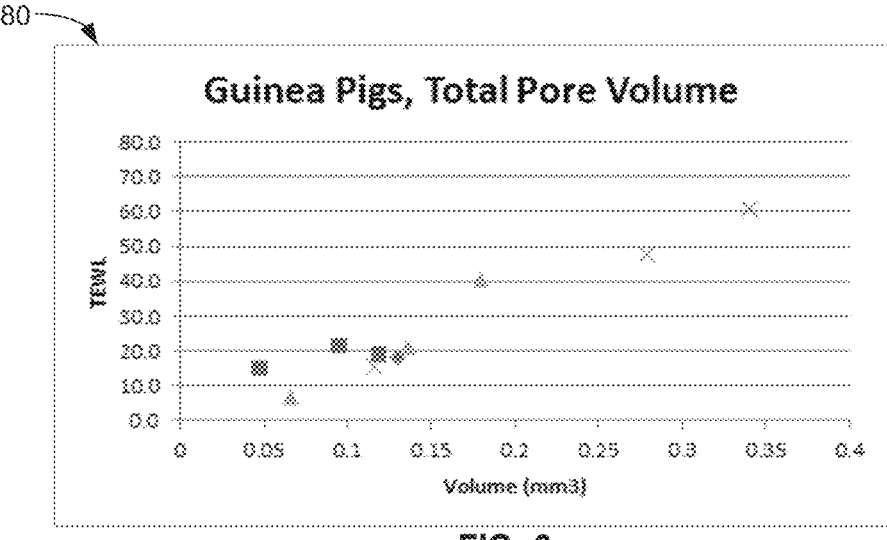

FIG. 6 is a graph 600 showing TEWL as a function of total pathway depth, a graph 640 showing TEWL as a function of total pathway area, and a graph 680 showing TEWL as a function of total pathway volume. The graph 600 data was measured using an artificial membrane (polyurethane). The graphs show a relationship between TEWL (in vivo hairless Guinea pig model) and measured total area in PU (top), measured total depth in PU (middle), and measured total depth in PU (bottom). The graph 600 shows TEWL along the y-axis and total pathway depth (for example, a sum of the depths of all pathways created by the microporation device 101) into polyurethane in μm along the x-axis. The graph 640 shows TEWL along the y-axis and total pathway area (for example, a sum of the areas of all pathways created by the microporation device 101) in the polyurethane in mm$^2$ along the x-axis. The graph 680 shows TEWL along the y-axis and total pathway volume (for example, a sum of the volumes of all pathways created by the microporation device 101) in the polyurethane in mm$^3$ along the x-axis.

The graphs 600, 640, and 680 show that with the average filaments 200 volume of 300,000 μm$^3$, using the filaments 200 formed from stainless steel having the width of 50 μm, length of 400 μm, and depth of 15 μm, between approximately 100 and 400 pathways are formed in the skin in about 2.5-10% of the area of the skin to which the filaments 200 are exposed when approximately 5 mJ/filament of energy is applied. The graph 600 shows that for different depths of pathways, different levels of TEWL are obtained. The graph 600 shows that as the depths increase, the TEWL increases. The graph 640 shows that for different areas of pathways, different levels of TEWL are obtained. The graph 640 shows that as the total area increases, the TEWL increases. The graph 680 shows that for different volumes of pathways, different levels of TEWL are obtained. The graph 680 shows that as the total volume increases, the TEWL increases.

Thus, TEWL correlates with the total pathway depth, the total pathway area, and the total pathway volume. The total pathway volume may be most related to the TEWL. The optimal total pathway volume may be between approximately 0.05 and 0.35 mm$^3$ per square centimeter of skin opposed to the filaments 200. In some embodiments, the total pathway depth may be between approximately 2500 and 30000 μm.

Figure 7:
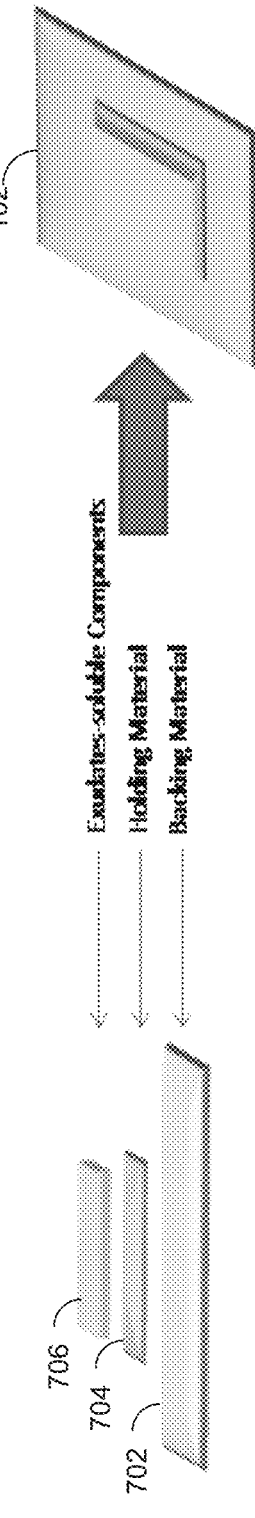
FIG. 7 shows a top perspective view of the transdermal patch 102.

FIG. 7 shows a top perspective view of the transdermal patch 102. The patch 102 may comprise a plurality of layers, for example a backing material layer 702, a holding material layer 704, and an exudate layer 706. The backing material layer 702 may form a "pocket" in which the holding material layer 704 and the exudate layer 706 sit while the backing material layer 702 attaches or couples the patch 102 to the skin.

The patch 102 may provide for controlled drug release and diffusion for large molecule delivery into the body of the patient. The polymer matrix may be optimized to enable efficient and control release and delivery of the drugs. Such optimization may comprise generating the polymer matrix to include or comprise a fiber. In some embodiments, the fiber may be nonwoven. Additionally, an optimized polymer matrix may comprise a matrix that is formed from a laminated material of film and fiber. In some embodiments, the fiber in the polymer matrix has a thickness of less than 300 μm or a thickness of less than 200 μm. In some embodiments, the fiber in the polymer matrix has a weight of less than 100 g per square meter of the fiber or less than 20 g per square meter of the fiber. In some embodiments, the permeant in the polymer matrix is between approximately 0.01 and 20 milligrams (mg) per square centimeter of skin to which the patch is exposed (mg/cm²). Furthermore, the polymer matrix may have a polymer matrix may have a water-holding capacity of less than 10 mg per square centimeter of skin.

The patch 102 provides for an immediate release of small to large molecule drugs through at least one pathway formed via the microporation device 101. The patch 102 releases a predetermined amount of the drug from the exudate layer 706. In some embodiments, the related, predetermined amount of the exudate in the exudate layer 706 comprises between approximately 0 mg/cm² and 85 mg/cm². In some embodiments, the predetermined amount of exudate released comprises between approximately 9.5 mg/cm² and 85 mg/cm². The exudate, when conveyed into the body via the pathways formed by the microporation device 101 dissolves the permeant and immediately releases the drug into the body, for example, into the bloodstream.

The exudate layer 706 may comprise a predetermined amount of exudates-soluble components (for example, about 0.1-20 mg/cm²) and a holding material. The pre-determined amount of exudates-soluble components may be used to adjust the amount of exudate delivered by the patch 102.

The holding material layer 704 may comprise a holding material having an optimal water-holding capacity ("WHC"). In some embodiments, the optimal WHC is selected to maximize a permeant delivery by the patch 102. In some embodiments, the optimal WHC is less than 10 mg/cm². The weight of the holding material in the holding material layer 704 may be less than 100 g/m², less than 30 g/m², or less than 20 g/m². The thickness of the holding material layer 704 may be less than 100 µm or less than 60 µm.

In some embodiments, various factors or aspects of the patch 102 may be optimized and/or controlled to maintain controlled, effective, and efficient drug delivery to the body via the skin when used in combination with the microporation device 101. For example, as described above, the exudate layer 706 may comprise a predetermined amount of exudates between about 10 and 85 mg/cm². In some embodiments, a total amount of exudates-soluble components loaded onto the patch 102 is in the range of approximately 0.1-20 mg/cm². In some embodiments, the holding material in the holding material layer 704 has the WHC in the range of about 0-10 mg/cm² and the weight density of less than 100 g/m² or less than 20 g/m². In some embodiments, the holding material has a non-woven thickness of less than 300 µm or 200 µm. In some embodiments, the backing material of the backing material layer 702 has an adhesive on one side to protect exudates leakage from the patch 102.

Figure 8:
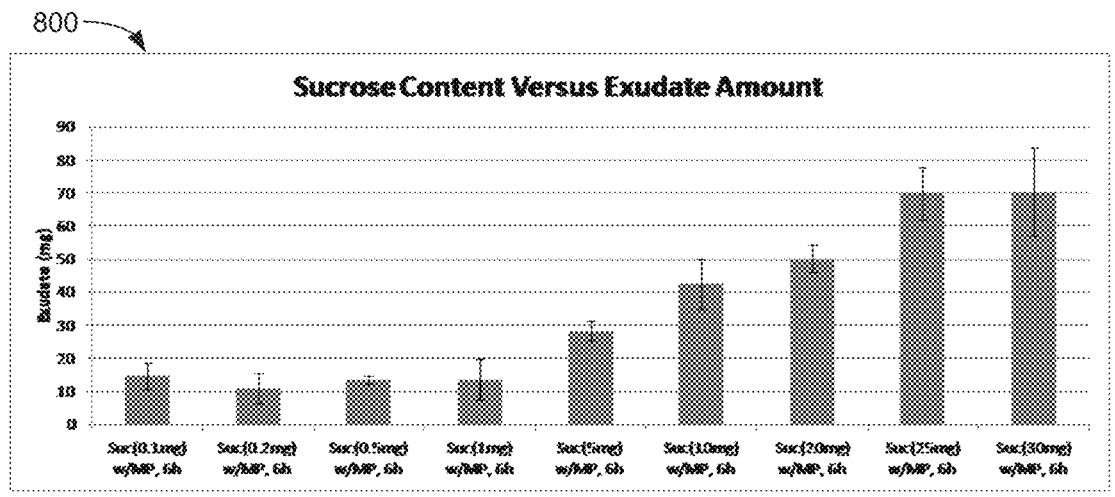
FIG. 8 is a graph 800 showing a sucrose content versus an exudate amount extracted from the patch 102 and a graph 840 showing an amount of exudate extraction of 2 patch formulations of sucrose compared under different applicator conditions.
Figure 8:
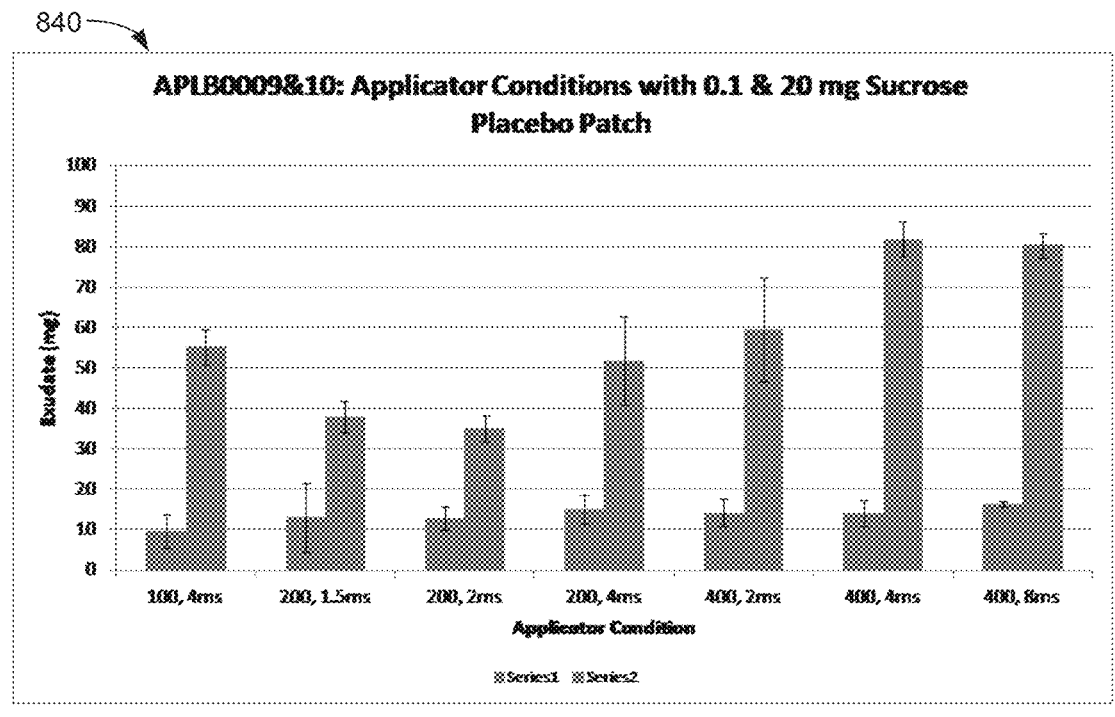

FIG. 8 is a graph 800 showing a sucrose content versus an exudate amount extracted from the patch 102 and a graph 840 showing an amount of exudate extraction of 2 patch formulations of sucrose compared under different applicator conditions.

The graph 800 shows the amount of exudate extracted in mg on the y-axis for a plurality of patches 102 with different levels of sucrose, shown along the x-axis. Each of the patches 102 shown in the graph 800 have different quantities of sucrose and are applied to skin having 200 pathways created via microporation at 2 ms pulse conditions. The patches 102 are left in place for 6 hours after application. The graph 800 shows the amount of exudate extracted from each patch 102. The graph 800 shows that, generally, as the amount of sucrose on the patch increases (from about 0.1 mg to 25 mg), the amount of exudate extracted also increases (from about 15 mg to about 70 mg). Thus, when the microporation parameters are maintained (200 pathways formed the same way for all patches 102), the concentration of the drug on the patch 102 controls the amount of exudate extracted from the body.

The graph 840 shows how variations in the microporation can change amounts of exudate that are extracted from the body. The graph 840 shows extracted exudate amounts in mg on the y-axis. The graph 840 includes pairs of patch 102 formulations with 0.1 and 20 mg of sucrose compared under different applicator conditions, where the applicator conditions correspond to variations in the microporation along the x-axis. For example, the different microporation variations include: 1) 100 pathways formed with 4 ms energy pulses; 2) 200 pathways formed with 1.5 ms energy pulses; 3) 200 pathways formed with 2 ms energy pulses; 4) 200 pathways formed with 4 ms energy pulses; 5) 400 pathways formed with 2 ms energy pulses; 6) 400 pathways formed with 4 ms energy pulses; and 7) 400 pathways formed with 8 ms pulses. As shown in graph 840, for the patch 102 formulation of 0.1 sucrose, the amount of exudate extracted from the body generally increases as the number of pathways increases or the duration of the energy pulses increases. However, the graph 840 shows that the amounts of exudate extracted from the 20 mg patch 102 varies more greatly as the number of pathways increases or the duration of the energy pulses increases.

Different materials have different water holding capacities and/or capabilities. The water holding capacity (WHC) of the matrix refers to the amount of moisture the matrix can hold per 1 cm². For example, a 1 cm² matrix is prepared, and this is immersed in a solution (phosphate buffered saline containing 0.1% surfactant (Tween 80)) for a sufficiently long amount of time. Following this, the matrix is slowly pulled out of the solution for around five seconds, the weight of the sample before immersion measured in advance is subtracted from the weight of the sample holding the liquid, and then it is possible to determine the water holding capacity of the matrix per unit area (1 cm²). In some embodiments, the matrix has a water holding capacity of 10 mg/cm² or less. In some embodiments, the matrix has a water holding capacity of 1 mg/cm² to 10 mg/cm². In an example, Tween 80 (Spectrum Chemical Mfg. Corp. or Croda), which had been weighed, was dissolved in phosphate buffered saline (Sigma-Aldrich), thereby preparing a 0.1 w/v % Tween 80-containing PBS (hereinafter called the test solution). The thickness of the matrix material was measured according with a digital indicator (U30A, manufactured by Sony Corporation). Matrix materials 1 to 3 (all manufactured by Japan Vilene Company, Inc.) shown in Table 1A were formed into 10 mm×10 mm squares, thereby preparing samples. The prepared samples were weighed, thereby obtaining their dry weights (hereinafter called weight A). Next, the foregoing samples were immersed in the test solution and fully impregnated with the test solution. The samples impregnated with the solution were slowly pulled out from the test solution (approximately 5 seconds/cm) and weighed, thereby obtaining their weight after test solution impregnation (hereinafter called weight B). Note that in the case where the matrix material has a film surface, it is weighed after the test solution adhered to the film surface after being pulled out has been wiped off, thereby obtaining weight B. Note that the thickness of the matrix material, weight A, and weight B were each measured three times, and the average values were adopted as the final values. The results are shown in Table 1A (below).

TABLE 1A

| Matrix Material | Product Number | Base Material | Weight $(g/m^2)$ | Thickness $(\mu m)$ | Property | Water Holding Capacity $(mg/cm^2)$ |
|---|---|---|---|---|---|---|
| 1 | EH-1212 | PET film/PET non-woven fabric | 12 | 38 | Hydrophilic | 4 |
| 2 | EW-0450 | ET film/PET non-woven fabric | 50 | 336 | Hydrophilic | 30 |
| 3 | EW-2080S | Polyester non-woven fabric | 80 | 600 | Hydrophobic | 55 |

As such, different materials may be used for the water holding material layer 704 of the patch 102. Water holding materials with WHC less than 10 $mg/cm^2$ may release permeants more quickly under controlled optimal amount of exudates extraction than water holding materials having a WHC greater than 10 $mg/cm^2$. In some embodiments, the pharmacokinetics (PK) results of the microporation drug delivery system for the delivery of small molecule to large molecule compounds show that for a water holding material's WHC, weights and thicknesses of the water holding material and weights of the exudates-soluble components are parameters that can optimize PK profiles for the particular drugs and/or patches 102. By maintaining these parameters within the ranges described above, the patches 102 can be used in the microporation drug delivery system to effectively and efficiently release drugs into the body in a controlled manner.

Figure 9:
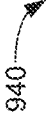
FIG. 9 is a graph 900 showing how the weight density of the water holding material impacts the WHC of the water holding material and a graph 940 showing how the thickness of the water holding material impacts the WHC of the water holding material.
Figure 9:
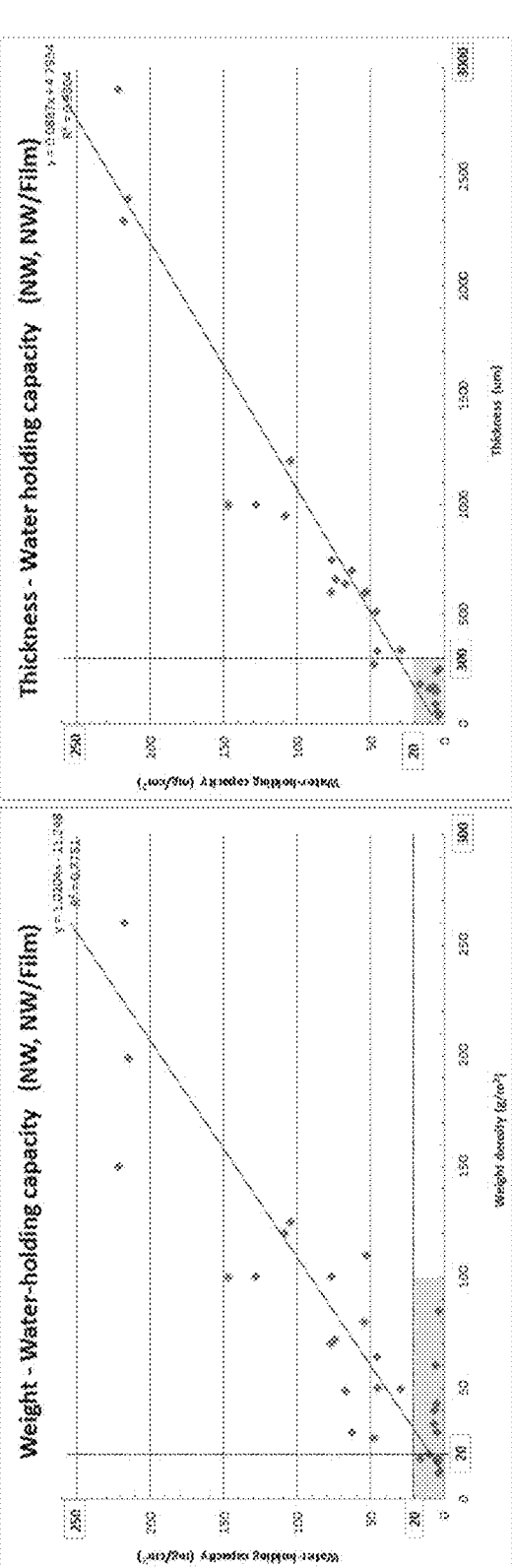

FIG. 9 is a graph 900 showing how the weight density of the water holding material impacts the WHC of the water holding material and a graph 940 showing how the thickness of the water holding material impacts the WHC of the water holding material.

The graph 900 shows the WHC along the y-axis that is a function of the weight density in $g/m^2$ shown along the x-axis. The graph 900 shows that generally, the WHC of the water holding material increases linearly as the weight density of the water holding material increases. The graph 900 includes a shaded portion representing water holding materials having low WHCs and small weight densities.

The graph 940 shows the WHC along the y-axis that is a function of the thickness in $\mu m$ shown along the x-axis. The graph 940 shows that generally, the WHC of the water holding material increases linearly as the thickness of the water holding material increases. The graph 940 includes a shaded portion representing water holding materials having low WHCs and small thicknesses.

As described above, the water holding material used in the patch 102 should have a WCH in the range of about 0-10 $mg/cm^2$, a weight density of less than 100 $g/m^2$ or less than 20 $g/m^2$, and a non-woven thickness of less than 300 $\mu m$ or less than 200 $\mu m$ to enable the efficient, effective, and controlled administration of drugs to the body via the pathways in the skin.

As described above, an effectiveness and/or selection of microporation parameters of the delivery of the drug via the microporation drug delivery system may depend on the drugs being administered by the patch 102. Various aspects of the drug and/or the microporation drug delivery system may impact the effectiveness of the drug, where the effectiveness corresponds to a bioavailability of the drug in the body. As described above, a combination of the microporation factors or parameters (for example, energy applied to the filaments 200, filament material, number of pathways created using the microporation device 101, an area of the skin in which the pathways are created and a treated area (in percentage of pathways per square centimeter of skin treated)) may impact the bioavailability of the drug after administration. Additionally, a combination of the patch 102 parameters (thickness, matrix parameters, weight, WHC, an active pharmaceutical ingredient ("API") weight in the patch 102, area of the patch) may impact the bioavailability of the drug after administration.

Table 1 below provides data of three groups of microporation values used to create pathways in the skin in hairless Guinea pigs before applying the patch 102 containing a long-acting peptide once weekly, for example Semaglutide. Table 2 below provides data of six (6) groups of drug administration: three (3) groups for the patch 102, one (1) group for oral administration of the long-acting peptide, and two (2) groups for injected administration of the long-acting peptide.

TABLE 1

| Group | Energy (mJ/filament) | Filament | Pores | Area | Treated Area |
|---|---|---|---|---|---|
| 1 | 5.2 | Stainless | 200 | 0.5 $cm^2$ | 10%/$cm^2$ |
| 2 | 5.2 | Stainless | 400 | 1.0 $cm^2$ | 10%/$cm^2$ |
| 3 | 5.2 | Stainless | 800 | 2.0 $cm^2$ | 10%/$cm^2$ |

TABLE 2

| Group | Matrix | Thickness $(\mu m)$ | Weight $(g/m^2)$ | WHC $(mg/cm^2)$ | Drug | Total Solid | Area |
|---|---|---|---|---|---|---|---|
| 1 | Nonwoven | 38 | 12 | 4 | 1 mg (2 $mg/cm^2$) | 3.25 mg (6.5 $mg/cm^2$) | 0.5 $cm^2$ |
| 2 | Nonwoven | 38 | 12 | 4 | 2 mg (2 $mg/cm^2$) | 6.5 mg (6.5 $mg/cm^2$) | 1.0 $cm^2$ |
| 3 | Nonwoven | 38 | 12 | 4 | 4 mg (2 $mg/cm^2$) | 13.0 mg (6.5 $mg/cm^2$) | 2.0 $cm^2$ |

TABLE 2-continued

| Group | Matrix | Thickness (μm) | Weight (g/m²) | WHC (mg/cm²) | Drug | Total Solid | Area |
|---|---|---|---|---|---|---|---|
| 4 | Sub Q | — | — | — | 0.5 mg | — | — |
| 5 | Sub Q | — | — | — | 1.0 mg | — | — |
| 6 | Oral | — | — | — | 2.0 mg | — | — |

Groups 1-3 in Tables 1 and 2 correspond to combinations of patches 102 and the microporation parameters for a particular administration. For example, the group 1 microporation parameters of Table 1 apply in conjunction with the administration of the patch 102 according to the parameters in Group 1 of Table 2. Accordingly, the patch 102 of group 1 has the nonwoven matrix, water holding material thickness of 38 μm, water holding material weight of 12 g/m², and WHC of 4 mg/cm³. The patch 102 of group 1 includes a drug of 1 mg and a total solid weight of 3.25 mg with an area of 0.5 cm². This patch 102 is applied to an area of the skin having 200 pathways created according to the group 1 microporation parameters, where the energy applied to the microporation device is 5.2 mJ/filament, the filaments 200 are made from stainless steel and have a treated area of 10% per square centimeter of skin, where the filaments 200 treat an area of 0.5 cm². Similarly, group 2 of the patch 102 parameters applies to group 2 of the microporation parameters and group 3 of the patch 102 parameters applies to group 3 of the microporation parameters. Groups 4 and 5 indicate that the drug of 0.5 mg and 1.0 mg are injected into the body and Group 6 indicates that the drug of 2.0 mg is consumed orally.

Figure 10:
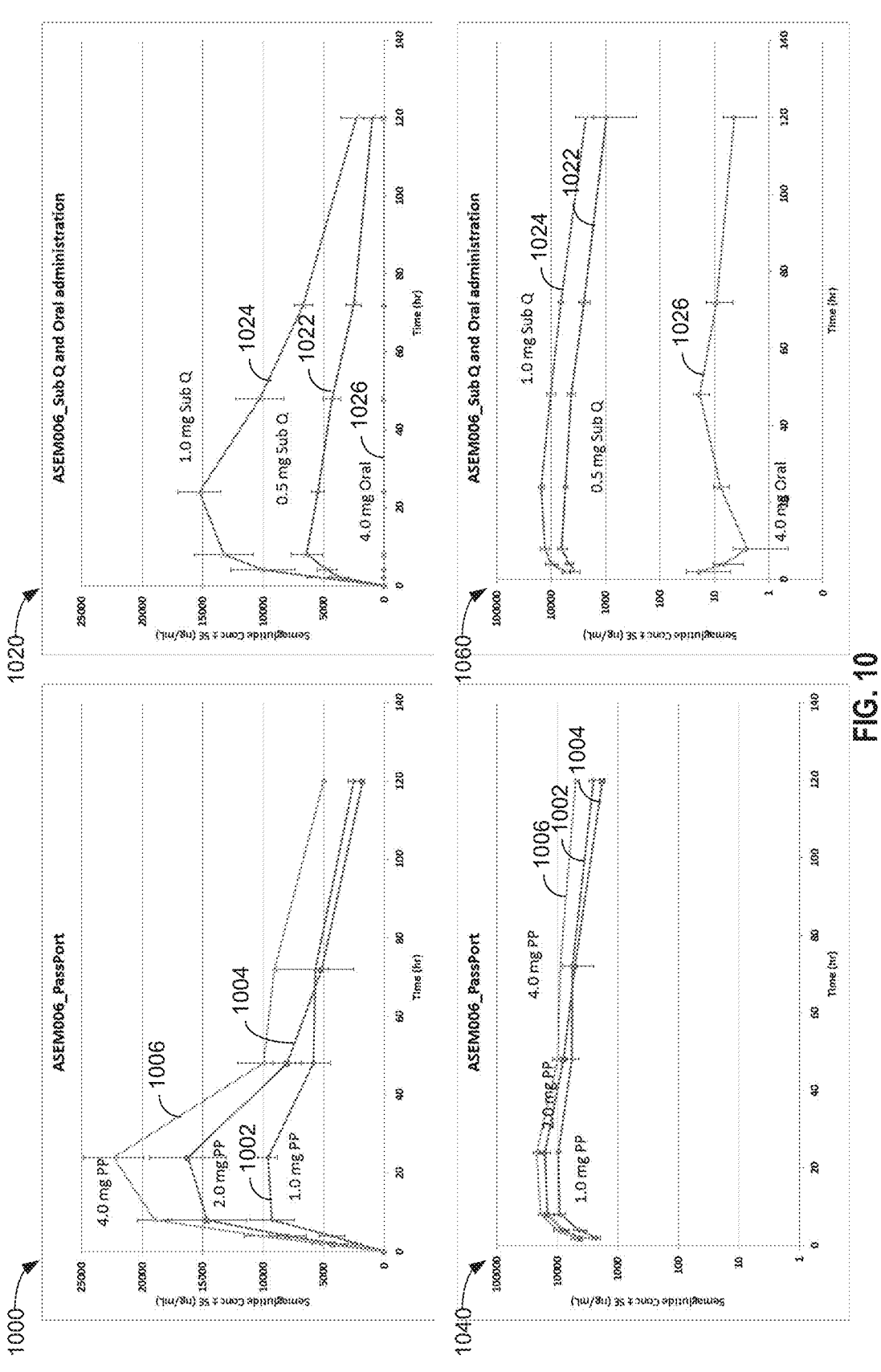
FIG. 10 shows graphs showing a comparison of the blood concentrations of the long-acting peptide for each of the groups 1-3 of microporation parameters and patch 102 parameters of Tables 1 and 2 and graphs showing a comparison of the concentrations of the long-acting peptide for each of the groups 4-6 within the body over time.

The graph 1000 in FIG. 10 shows a comparison of the concentrations of the long-acting peptide for each of the groups 1-3 of microporation parameters and patch 102 parameters of Tables 1 and 2. The graph 1000 includes the concentration of the long-acting peptide in nanograms/milliliter (ng/mL) along the y-axis and time in hours (hr) along the x-axis. The graph 1000 shows three lines 1002, 1004, and 1006. The line 1002 represents the group 1 microporation parameters and the group 1 patch 102 parameters. The line 1004 represents the group 2 microporation parameters and the group 2 patch 102 parameters. The line 1006 represents the group 3 microporation parameters and the group 3 patch 102 parameters. Each of the three lines 1002, 1004, and 1006 follow the same general trend. For each of the groups 1-3 of parameters, the concentrations of the long-acting peptide generally increase to a maximum concentration relatively quickly before gradually lessening, finally reaching a concentration of 0. The parameters of group 3 are shown by line 1006 to have the highest concentration level spike as well as the higher concentration value for the duration of the bioavailability of the long-acting peptide in the body as compared to the parameters of groups 1 and 2 shown by lines 1002 and 1004. While the parameters of group 2 are shown by line 1004 to have a higher concentration level spike than the parameters of group 2 shown by line 1002, the concentration level of the bioavailability of the long-acting peptide is actually higher for the group 1 parameters after approximately 70 hours (shown by line 1002 indicating a higher concentration value at times greater than approximately 70 hours).

The graph 1020 in FIG. 10 shows a comparison of the concentrations of the long-acting peptide for each of the groups 4-6 within the body over time. The graph 1020 includes the concentration of the long-acting peptide in nanograms/milliliter (ng/mL) along the y-axis and time in hours (hr) along the x-axis. The graph 1020 shows three lines 1022, 1024, and 1026. The line 1022 represents the group 4 injected drug. The line 1024 represents the group 5 injected drug. The line 1026 represents the group 6 injected drug. Each of the lines 1022 and 1024 follow the same general trend, rising to a highest level of concentration before gradually falling and approaching a concentration level of 0. The line 1026 shows that oral consumption of the long-acting peptide does not provide for any measurable concentration within the body. The parameters of group 5 are shown by line 1024 to have a higher concentration level spike for the duration of the bioavailability of the long-acting polypeptide in the body as compared to the parameters of group 4 shown by line 1022.

The graph 1040 is zoomed out view of the graph 1000, giving a higher level view of the relationships of the lines 1002, 1004, and 1006. Similarly, the graph 1060 is a zoomed out view of the graph 1020, showing that the line 1026 (oral consumption of the long-lasting peptide) hovers around a concentration of 10 ng/mL and is not 0, as it appears from the graph 1020.

Based on the graphs 1000, 1020, 1040, and 1060, the area under the curve for each of groups 1-6 is shown below in Table 3:

| Group | AUC (ng/ml*hr) | BA (%) |
|---|---|---|
| 1 | 512732.8 | 63.6 |
| 2 | 757592.5 | 47.0 |
| 3 | 1026596.5 | 31.8 |
| 4 | 329929.0 | 81.8 |
| 5 | 806568.00 | 100.0 |
| 6 | 789.83 | 0.0 |

Table 3 shows that the bioavailability of the long-acting peptide varies for each of the different administrations. While the injected administrations of groups 4 and 5 show the highest percentages of bioavailability, the administrations via the patches 102 of groups 1-3 are able to provide similar levels of concentration as the injected administrations of groups 4 and 5 via the microporation drug delivery system.

Table 4 below provides data of one group (group 1) of a patch 102 containing a long-acting protein, for example Etanercept, applied without any microporation, three groups (groups 2-4) of microporation values for use with patches 102, and one group (group 5) of injected administration of the long-acting protein. Table 5 below provides patch 102 details for the five groups of Table 4. Table 6 below provides details of the components of the patch or drug formulation administered according to the groups 1-5.

TABLE 4

| Group | Energy (mJ/filament) | Filament | Pores | Area | Treated Area |
|---|---|---|---|---|---|
| 1 | Without microporation | — | — | 1.0 cm2 | — |
| 2 | 5.2 | Stainless | 400 | 1.0 cm2 | 10%/cm2 |
| 3 | 5.2 | Stainless | 400 | 1,0 cm2 | 10%/cm2 |
| 4 | 5.2 | Stainless | 400 | 1,0 cm2 | 10%/cm2 |
| 5 | Sub Q | — | — | — | — |

TABLE 5

| Group | Matrix | Thickness (μm) | Weight (g/m$^2$) | WHC (mg/cm$^2$) | Drug | Total Solid | Area |
|---|---|---|---|---|---|---|---|
| 1 | Nonwoven | 38 | 12 | 4 | 5.0 mg (5.0 mg/cm$^2$) | 10 mg (10 mg/cm$^2$) | 1.0 cm$^2$ |
| 2 | Nonwoven | 38 | 12 | 4 | 5.0 mg (5.0 mg/cm$^2$) | 10 mg (10 mg/cm$^2$) | 1.0 cm$^2$ |
| 3 | Nonwoven | 38 | 12 | 4 | 5.0 mg (5.0 mg/cm$^2$) | 15 mg (15 mg/cm$^2$) | 1.0 cm$^2$ |
| 4 | Nonwoven | 38 | 12 | 4 | 5.0 mg (5.0 mg/cm$^2$) | 15 mg (15 mg/cm$^2$) | 1.0 cm$^2$ |
| 5 | Sub Q | | | | 1.0 mg | 1.0 mg | |

TABLE 6

| ingredients | G1 | G2 | G3 | G4 | G5 |
|---|---|---|---|---|---|
| Etanercept | 5.00 | 5.00 | 5.00 | 5.00 | 1.00 |
| Sucrose | 5.00 | 5.00 | 5.00 | 5.00 | |
| Urea | 0.00 | 0.00 | 5.00 | 0.00 | |
| Disodium citrate sesesquihydrate | 0.00 | 0.00 | 0.00 | 5.00 | |
| Solid Total (mg) | 10.00 | 10.00 | 15.00 | 15.00 | 1.00 |

TABLE 7

| Group | AUC (ng/ml*hr) | BA (%) | Cmax (ng/mL) |
|---|---|---|---|
| 1 | 172.0 | 0.0 | 9.6 |
| 2 | 208592.9 | 94.3 | 5189.0 |
| 3 | 604088.4 | 99.4 | 16578.6 |
| 4 | 712825.1 | 117.2 | 16982.4 |
| 5 | 121572.3 | 100.0 | 1298.7 | data of six (6) groups of drug administration: three (3) groups for the patch 102, one (1) group for oral administration of the long-acting peptide, and two (2) groups for injected administration of the long-acting peptide.

Figure 11:
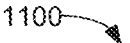
FIG. 11 shows graphs showing a comparison of the blood concentrations of the long-acting protein for each of the groups 1-5 of Tables 4-6.
Figure 11:
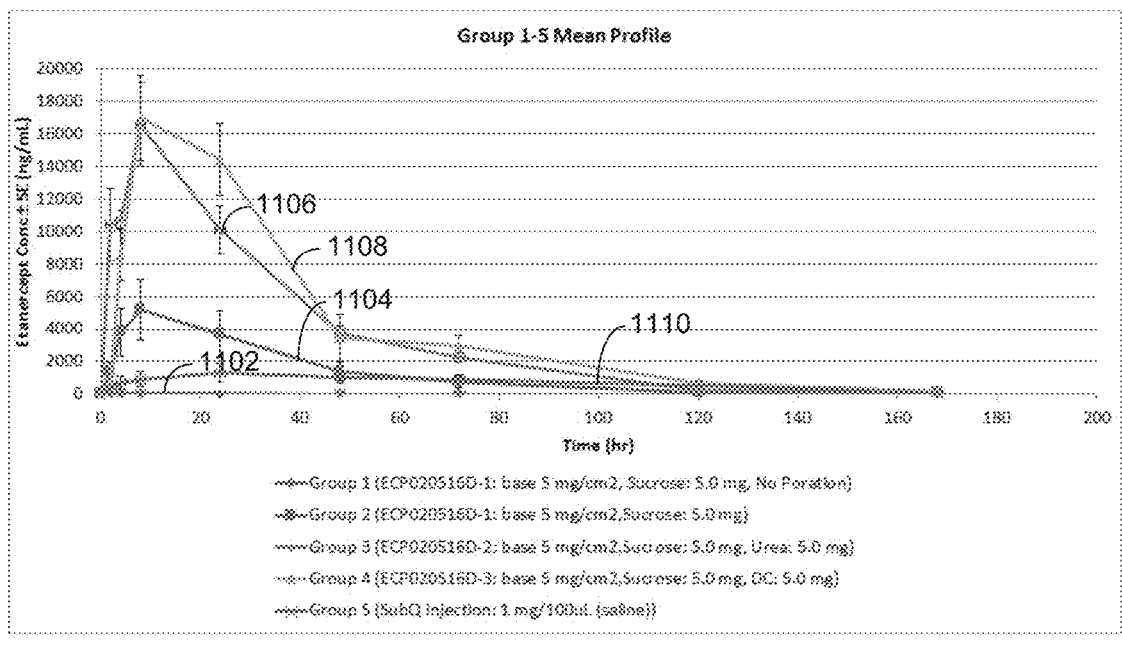
Figure 11:
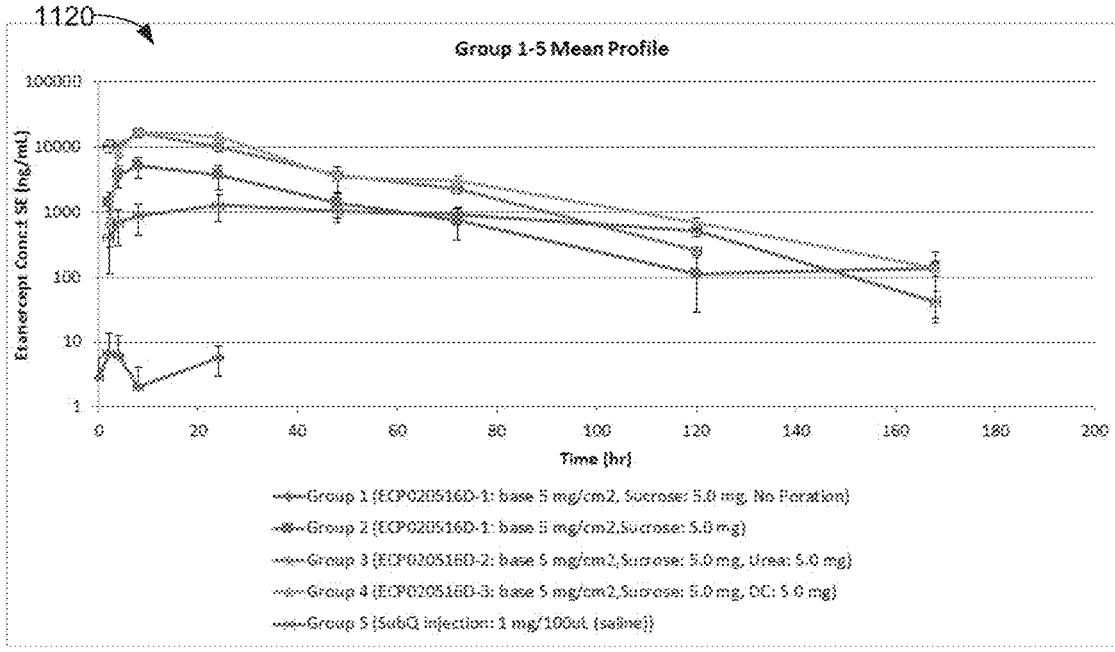

The graph 1100 in FIG. 11 shows a comparison of the concentrations of the long-acting protein for each of the groups 1-5 of Tables 4-6. The graph 1100 includes the concentration of the long-acting protein in nanograms/milliliter (ng/mL) along the y-axis and time in hours (hr) along the x-axis. The graph 1100 shows five lines 1102, 1104, 1106, 1108, and 1110. The line 1102 represents the group 1 patch 102 with no microporation. The line 1104 represents the group 2 microporation parameters and the group 2 patch 102 parameters. The line 1106 represents the group 3 microporation parameters and the group 3 patch 102 parameters. The line 1108 represents the group 4 microporation parameters and the group 4 patch 102 parameters. The line 1110 represents the injected long-acting protein. Each of the three lines 1104, 1106, and 1108 follow the same general trend. For each of the groups 2-4 of parameters, the concentrations of the long-acting protein generally increase to a maximum concentration relatively quickly before gradually lessening, finally reaching a concentration of 0. The parameters of groups 3 and 4 are shown by line 1106 and 1108 to have the highest concentration level spike while the group 4 parameters result in the higher long term concentration. The parameters of group 2 are shown by line 1104 to have a generally lower concentration levels throughout as compared to the groups 3 and 4 parameters. The group 1 and group 5 administrations are lower than all of the group 2-4 administrations. Thus, for the long-acting protein, the patch administration at skin locations treated with microporation result in better bioavailabilities than even the injected administration of the drug, as detailed in Table 7 below. The graphs 1100 and 1120 also show what effects the additional components in the drug formulation (for example, sucrose, urea, and so forth) may have on the bioavailability and blood concentrations of the long-acting protein in rats.

The graph 1120 is zoomed out view of the graph 1100, giving a higher level view of the relationships of the lines 1102, 1104, 1106, 1108, and 1110.

Based on the graphs 1100 and 1120, the area under the curve for each of groups 1-5 is shown above in Table 7. Table 7 shows that the bioavailability of the long-acting protein varies for each of the different administrations. The administrations using the patches 102 with the different microporation parameters are shown to result in the greatest concentration levels of the drug available for the longest durations.

Table 8 below provides data of two groups (groups 1 and 2) of microporation values for use with a patch 102 containing a long-acting protein, for example Etanercept. Table 9 below provides patch 102 details for the two groups of Table 8. Table 10 below provides details of the components of the patch or drug formulation administered according to the groups 1 and 2. As shown, both groups have the same drug formulation of the long-acting protein and sucrose in the same quantities.

TABLE 8

| Group | Energy (mJ/filament) | Filament | Pores | Area | Treated Area |
|---|---|---|---|---|---|
| 1 | 5.2 | Stainless | 400 | 1.0 cm$^2$ | 10%/cm$^2$ |
| 2 | 5.2 | Stainless | 400 | 1.0 cm$^2$ | 10%/cm$^2$ |

TABLE 9

| Group | Matrix | Thickness (μm) | Weight (g/m²) | WHC (mg/cm²) | Drug | Total Solid | Area |
|---|---|---|---|---|---|---|---|
| 1 | Nonwoven | 38 | 12 | 4 | 5.0 mg (5.0 mg/cm²) | 15 mg (15 mg/cm²) | 1.0 cm² |
| 2 | Nonwoven | 336 | 50 | 30 | 5.0 mg (5.0 mg/cm²) | 15 mg (15 mg/cm²) | 1.0 cm² |

TABLE 10

|  | G1 | G2 |
|---|---|---|
| Etenercept | 5.00 | 5.00 |
| Sucrose | 10.00 | 10.00 |
| Total Solid (mg) | 15.00 | 15.00 |

Figure 12:
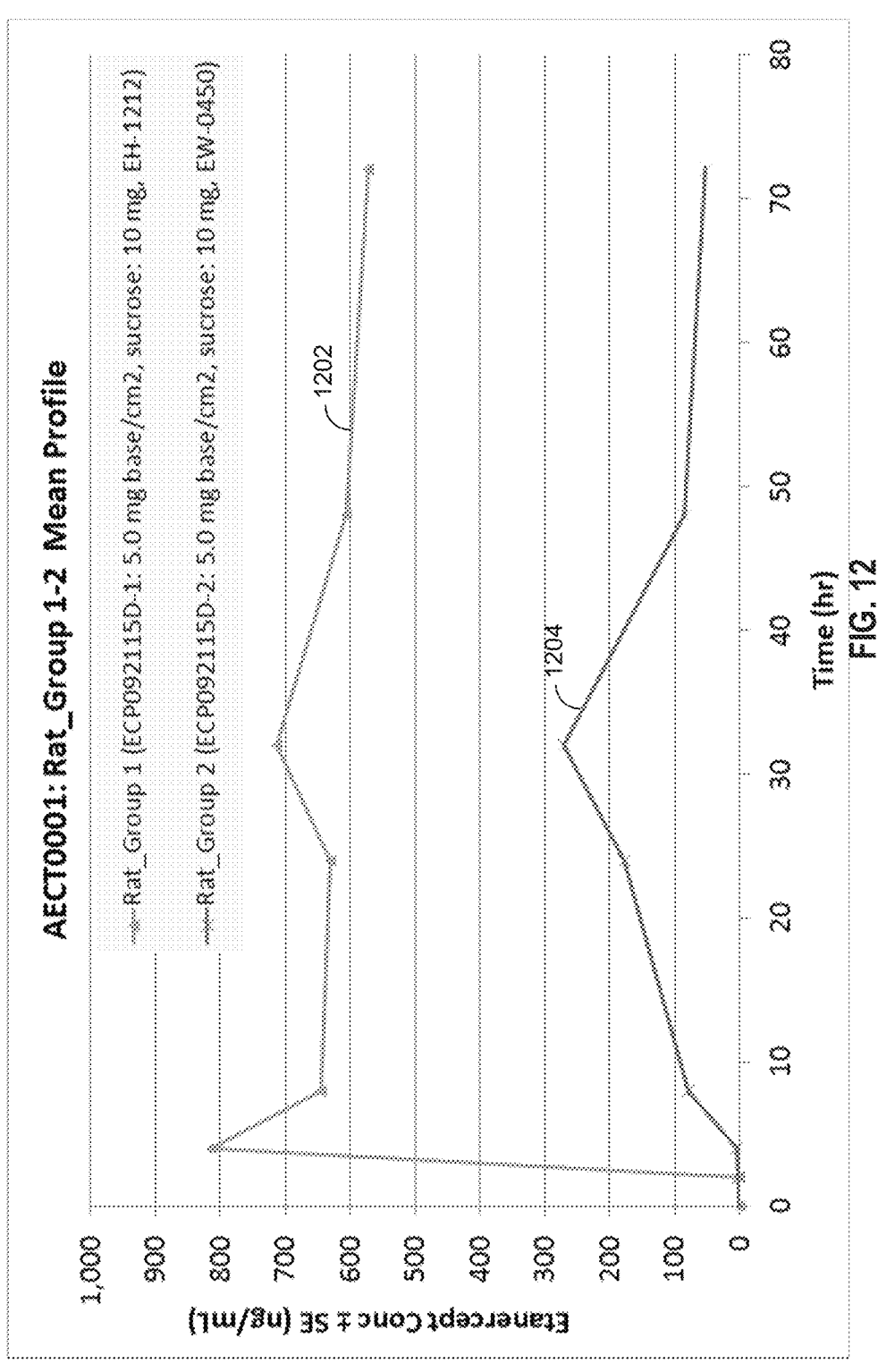
FIG. 12 shows a graph showing a comparison of the blood concentrations of the long-acting protein for each of the groups 1 and 2 of Tables 8-10.

The graph 1200 in FIG. 12 shows a comparison of the concentrations of the long-acting protein for each of the groups 1 and 2 of Tables 8-10. The graph 1200 shows the mean profile between the concentrations of the long-acting protein in rats. The graph 1200 includes the concentration of the long-acting protein in nanograms/milliliter (ng/mL) along the y-axis and time in hours (hr) along the x-axis. The graph 1200 shows two lines 1202 and 1204. The line 1202 represents the group 1 patch 102 with microporation parameter according to Table 8 and patch 102 parameters according to Table 9. The line 1204 represents the group 2 patch 102 with microporation parameter according to Table 8 and patch 102 parameters according to Table 9. The two lines 1202 and 1204 follow different trends. The line 1202 spikes quickly to a peak of above 800 ng/mL and then remains generally between 500 and 700 ng/mL until at least about 70 hours. The line 1204 gradually increases to a peak of about 275 ng/mL at about 32 hours before then decreasing to below 100 ng/mL at about 70 hours. This highlights the effects that the patch 102 parameters can have on the administration of the drug formulation.

Table 11 below provides molecular weights for exemplary permeants that may be used in the patches 102 of the microporation drug delivery system.

TABLE 11

| Permeants | | Molecular Weight |
|---|---|---|
| Polysaccharide | Fondaparinux | 1,728 |
| Peptide | Exenatide | 4,187 |
|  | Lixisenatide | 4,859 |
|  | Semaglutide | 4,114 |
|  | Teriparatide | 4,118 |
| Protein | Somatropin | 22,124 |
| Antigen | Ovalbumin | approximately 43,000 |
| Antibody/Fc Protein | Eternacept | approximately 150,000 |

Details regarding the use of these permeants (for example, amounts applied to the patch 102 when used with the microporation drug delivery system are provided below.

Figure 13:
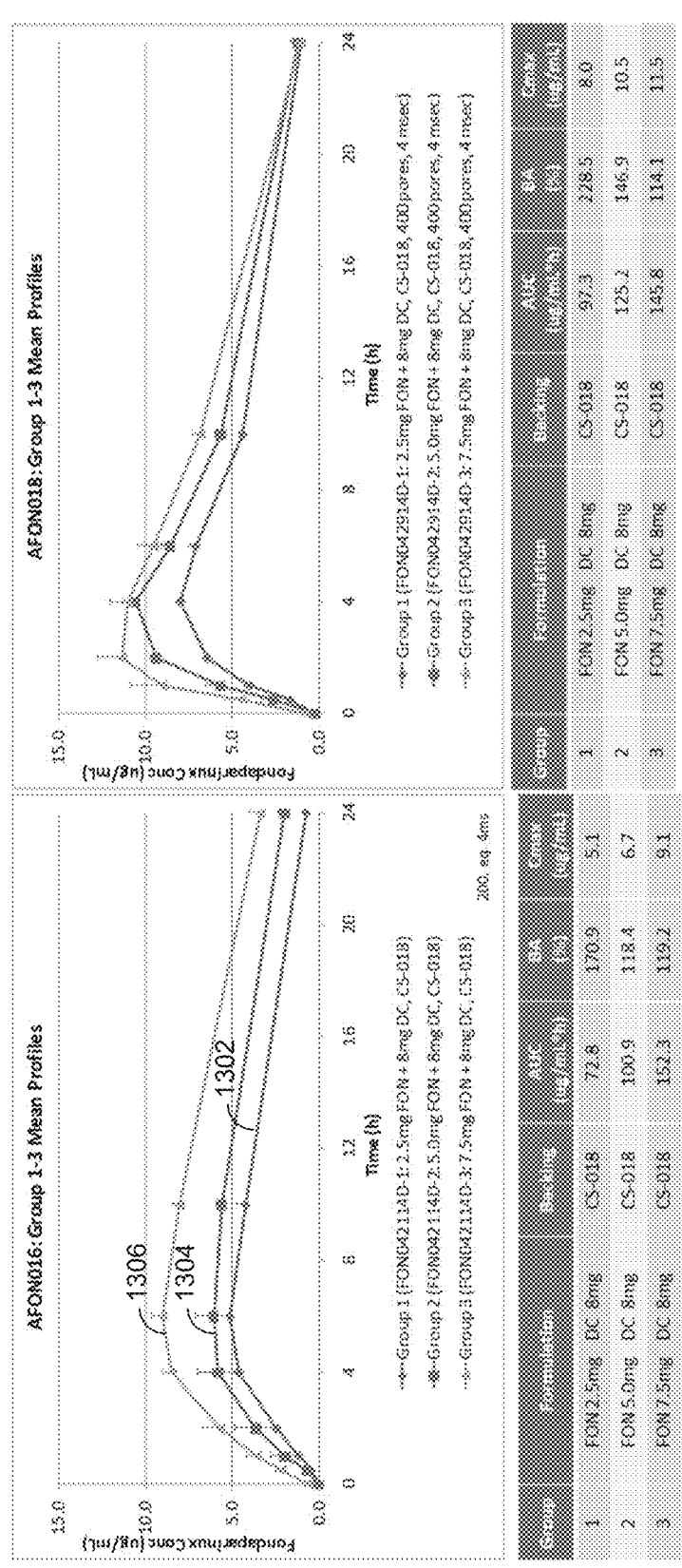
FIG. 13 shows a graph showing a comparison of the blood concentration levels in hairless Guinea pigs when a polysaccharide is the type of drug formulation applied to the patch 102 and a graph showing the mean profiles for the polysaccharide described above for 400 pathways generated at 4 ms pulses, as described above.

The graph 1300 in FIG. 13 shows a comparison of the concentration levels in hairless Guinea pigs when a polysaccharide is the type of drug formulation applied to the patch 102. The patch 102 used for FIG. 13 graphs 1300 and 1320 has a nonwoven matrix, a thickness of 180 μm, weight of 18 g/m², WHC of 17 mg/cm², a drug of 0.01 mg/cm², and a total solids level of 6.1 mg/cm². An energy pulse of 6.3 mJ and 5.2 mJ per filament to create between about 200 and 400 pathways via microporation having a 1 cm² treated area of between about 5 and 10% per square centimeter of skin, respectively.

The graph 1300 shows the mean profiles for the polysaccharide described above for 200 pathways generated at 4 ms pulses, as described above. The graph 1300 includes the concentration of the polysacharride (for example, Fondaparinux) in micrograms/milliliter (μg/mL) along the y-axis and time in hours (hr) along the x-axis. The graph 1300 shows three lines 1302, 1304, and 1306. The line 1302 represents the patch 102 having a formulation of 2.5 mg of the polysacharride applied with the patch 102 and microporation parameters described above. The line 1304 represents the patch 102 having a formulation of 5.0 mg of the polysacharride applied with the patch 102 and microporation parameters described above. The line 1306 represents the patch 102 having a formulation of 7.5 mg of the polysacharride applied with the patch 102 and microporation parameters described above. Each of the three lines 1302, 1304, and 1306 follow the same general trend of increasing to a peak concentration value and then gradually decreasing in concentration. The line 1306 has the highest concentration values, followed by line 1304 and then line 1302. The line 1302 has an area under the curve (AUC) of 72.8 μg/mL*h, a bioavailability of 170.9%, and a maximum concentration of 5.1 μg/mL. The line 1304 has an AUC of 100.9 μg/mL*h, a bioavailability of 118.4%, and a maximum concentration of 6.7 μg/mL. The line 1306 has an AUC of 152.3 μg/mL*h, a bioavailability of 119.2%, and a maximum concentration of 9.1 μg/mL.

The graph 1320 shows the mean profiles for the polysaccharide described above for 400 pathways generated at 4 ms pulses, as described above. The graph 1320 includes the concentration of the polysacharride (for example, Fondaparinux) in micrograms/milliliter (μg/mL) along the y-axis and time in hours (hr) along the x-axis. The graph 1320 shows three lines 1322, 1324, and 1326. The line 1322 represents the patch 102 having a formulation of 2.5 mg of the polysacharride applied with the patch 102 and microporation parameters described above. The line 1324 represents the patch 102 having a formulation of 5.0 mg of the polysacharride applied with the patch 102 and microporation parameters described above. The line 1326 represents the patch 102 having a formulation of 7.5 mg of the polysacharride applied with the patch 102 and microporation parameters described above. Each of the three lines 1322, 1324, and 1326 follow the same general trend of increasing to a peak concentration value and then gradually decreasing in concentration. The line 1326 has the highest concentration values, followed by line 1324 and then line 1322. The line 1322 has an AUC of 97.3 μg/mL*h, a bioavailability of 228.5%, and a maximum concentration of 8.0 μg/mL. The line 1324 has an AUC of 125.2 μg/mL*h, a bioavailability of 146.9%, and a maximum concentration of 10.5 μg/mL. The line 1326 has an AUC of 145.8 μg/mL*h, a bioavailability of 114.1%, and a maximum concentration of 11.5 μg/mL.

The comparison of graphs 1300 and 1320 show how the increase in the number of pathways can improve the concentrations of the polysaccharide in hairless Guinea pigs.

Figure 14:
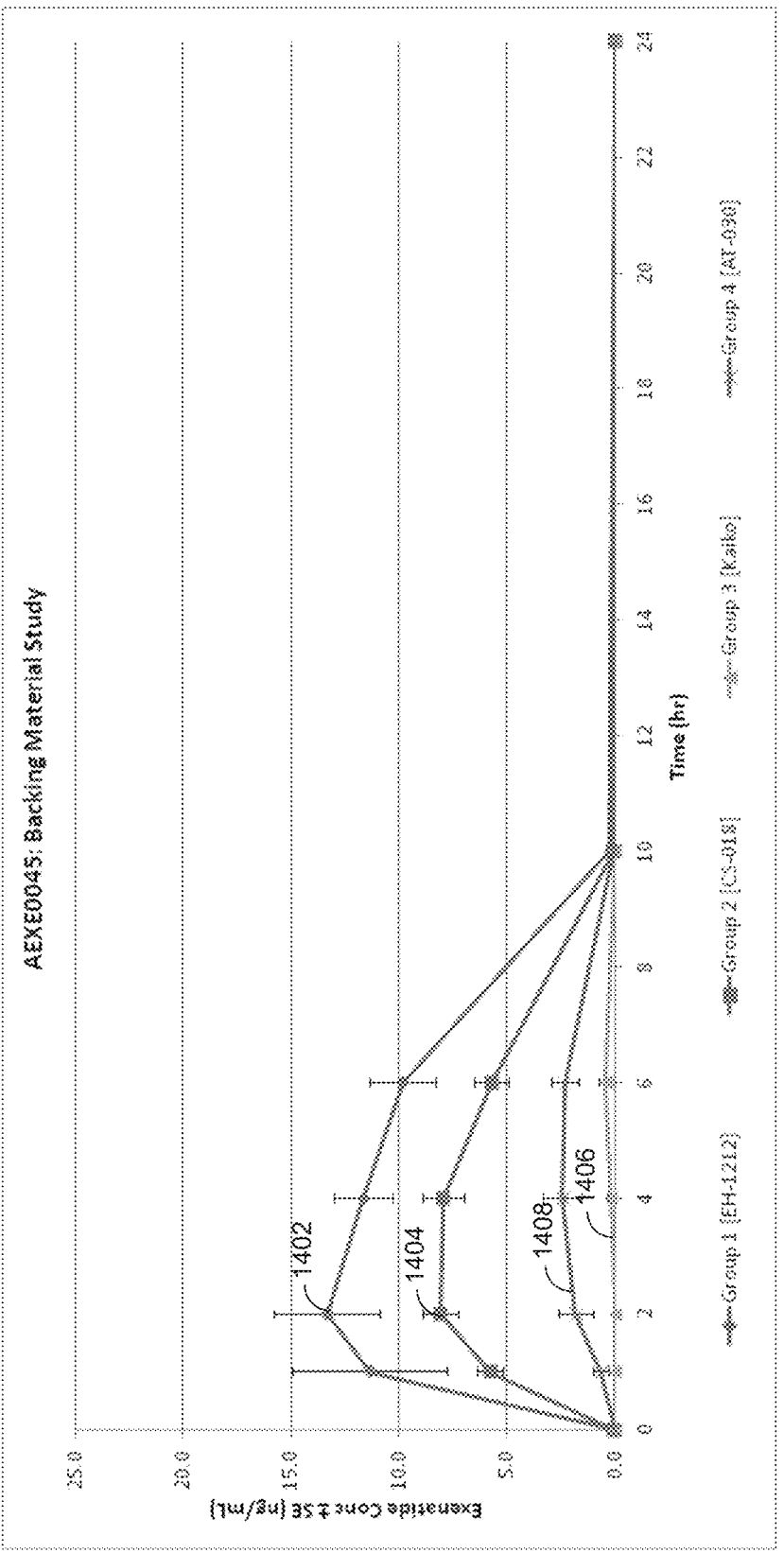
FIG. 14 shows a graph showing a comparison of the blood concentration levels in hairless Guinea pigs when a peptide is the type of drug formulation applied to the patch 102 with four groups of patches 102 having different patch parameters.

The graph 1400 in FIG. 14 shows a comparison of the blood concentration levels in hairless Guinea pigs when a peptide is the type of drug formulation applied to the patch 102 with four groups of patches 102 having different patch parameters. The patch 102 parameters are provided below in Table 12.

TABLE 12

| Group | Matrix | Thickness (μm) | Weight (g/m²) | WHC (mg/cm²) | Drug (mg/cm²) | Total Solid (mg/cm²) |
|---|---|---|---|---|---|---|
| G1 | Nonwoven | 38 | 12 | 4 | 0.1 | 1.1 |
| G2 | Nonwoven | 18 | 180 | 17 | 0.1 | 1.1 |
| G3 | Nonwoven | 70 | 600 | 77 | 0.1 | 1.1 |
| G4 | Nonwoven | 30 | 700 | 63 | 0.1 | 1.1 |

An energy pulse of 6.3 mJ per filament to create between about 200 pathways via microporation having a treated area of about 5% per square centimeter of skin.

The graph 1400 shows the backing materials study for the peptide (for example, Exenatide) described above for 200 pathways generated at 4 ms pulses, as described above. The graph 1400 includes the concentration of the peptide in ng/mL along the y-axis and time in hours (hr) along the x-axis. The graph 1400 shows four lines 1402, 1404, 1406, and 1408. The line 1402 represents the patch 102 having the patch 102 parameters of group G1 of Table 12 and the microporation parameters described above. The line 1404 represents the patch 102 having the patch 102 parameters of group G2 of Table 12 and the microporation parameters described above. The line 1406 represents the patch 102 having the patch 102 parameters of group G3 of Table 12 and microporation parameters described above. The line 1408 represents the patch 102 having the patch 102 parameters of group G4 of Table 12 and microporation parameters described above. Each of the four lines 1402, 1404, 1406, and 1408 follow the same general trend of increasing to a peak concentration value and then gradually decreasing in concentration. The line 1402 has the highest concentration values, followed by line 1404, then line 1406, and finally line 1408.

Graph 1400 shows that having greater WHC (for example, greater than 30 g/m² weight density) actually reduces the drug delivery effectiveness of the patch 102 as compared to lower WHC (for example, lower than 20 g/m²). The line 1402 has an AUC of 86.275 ng/mL*h, a bioavailability of 75.284%, and a maximum concentration of 14.317 ng/mL. The line 1404 has an AUC of 51.583 μg/mL*h, a bioavailability of 45.011%, and a maximum concentration of 8.996 ng/mL. The line 1406 has an AUC of 1.714 ng/mL*h, a bioavailability of 1.496%, and a maximum concentration of 0.438 ng/mL. The line 1408 has an AUC of 15.643 ng/mL*h, a bioavailability of 13.650%, and a maximum concentration of 2.849 ng/mL.

Figure 15:
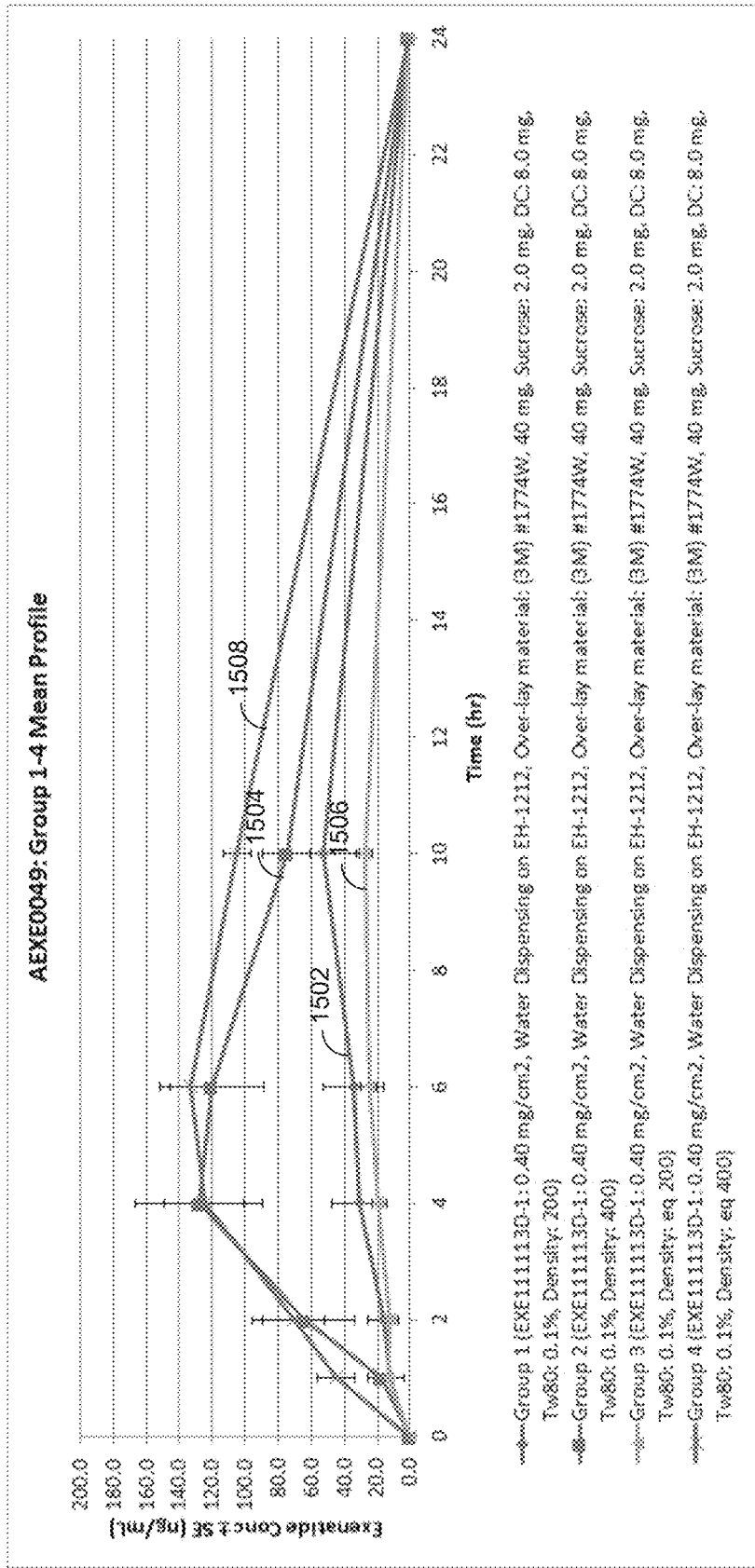
FIG. 15 shows a graph showing a comparison of the blood concentration levels in hairless Guinea pigs when a peptide is the type of drug formulation applied to the patch 102.

The graph 1500 in FIG. 15 shows a comparison of the blood concentration levels in hairless Guinea pigs when a peptide is the type of drug formulation applied to the patch 102.

The microporation occurs with a stainless steel filament 200 having applied thereto an energy pulse of 6.3 mJ and 5.2 mJ per filament to create between about 200 and 400 pathways with a treated area of between about 5 and 10% per square centimeter of skin. The patch 102 used for the administration of the peptide shown in graph 1500 has a thickness of 38 μm, a weight of 12 g/m², a WHC of 4 mg/cm², an API of 0.4 mg/cm², and a total solid weight of 10.4 mg/cm². Groups 2 and 4 apply to a treated area of 10%/cm² and groups 1 and 3 apply to a treated area of 5%/cm².

The graph 1500 shows the mean profile for the peptide (for example, Exenatide) described above for either 200 or 400 pathways and either 5%/cm² or 10%/cm² treated area, generated at 4 ms pulses, as described above. The graph 1500 includes the concentration of the peptide in ng/mL along the y-axis and time in hours (hr) along the x-axis. The graph 1500 shows four lines 1502, 1504, 1506, and 1508. The line 1502 represents the patch 102 having the microporation parameters of 200 pathways at 5%/cm² treated area. The line 1504 represents the patch 102 having the microporation parameters of 400 pathways at 10%/cm² treated area. The line 1506 represents the patch 102 having the microporation parameters of 200 pathways at 5%/cm² treated area (note: density 100 but wide filament equivalent to density 200). The line 1508 represents the patch 102 having the microporation parameters of 500 pathways at 10%/cm² treated area (note: density 200 but wide filament equivalent to density 400). Each of the four lines 1502, 1504, 1506, and 1508 follow the same general trend of increasing to a peak concentration value and then gradually decreasing in concentration. The line 1508 generally has the highest concentration values, followed by line 1502, then line 1502, and finally line 1506.

Based on the graph 1500, the area under the curve for each of groups 1-4 is shown below in Table 13. Table 13 shows that the bioavailability of the peptide varies for each of the different administrations. The administration of group 1 results in an AUC of 509.247 ng/mL*hr and a bioavailability of 20.282%. The administration of group 2 results in an AUC of 1416.218 ng/mL*hr and a bioavailability of 56.404%. The administration of group 3 results in an AUC of 407.298 ng/mL*hr and a bioavailability of 16.221%. The administration of group 4 results in an AUC of 1757.651 ng/mL*hr and a bioavailability of 70.002%. Thus, the graph 1500 shows that the delivery of peptides may be related to pathway density and the pharmacokinetics (PK) is also correlated to total pathway area, which may be related to the shape of the filament 200.

TABLE 13

| Group | AUC (ng/ml*hr) | BA |
|---|---|---|
| 1 | 509.247 | 20.282 |
| 2 | 1416.218 | 56.404 |
| 3 | 407.298 | 16.221 |
| 4 | 1757.651 | 70.002 |

Figure 16:
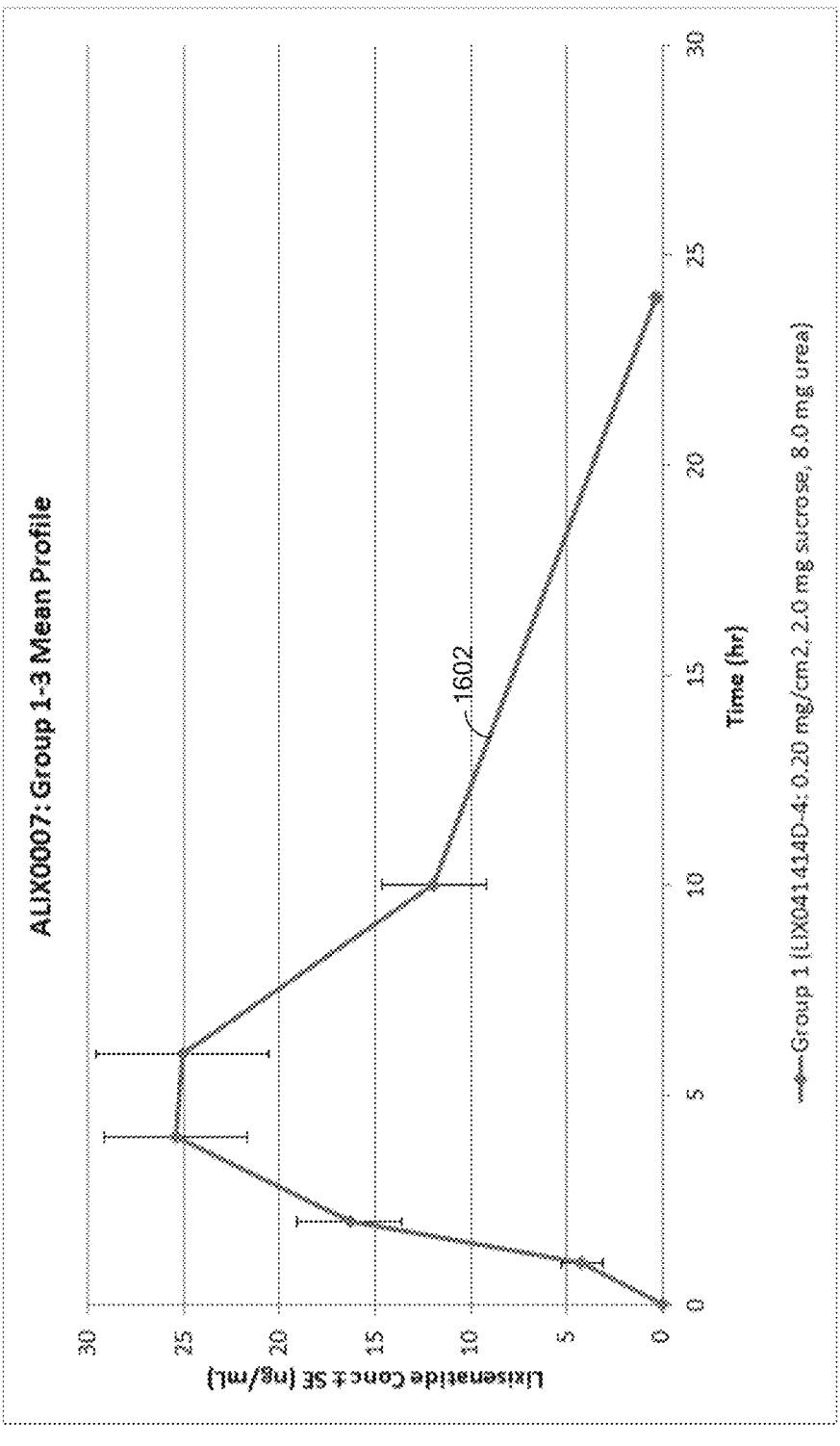
FIG. 16 shows a graph showing blood concentration levels in hairless Guinea pigs when a peptide (for example, Lixisenatide) is the type of drug formulation applied to the patch 102.

The graph 1600 in FIG. 16 shows concentration levels in hairless Guinea pigs when a peptide (for example, Lixisenatide) is the type of drug formulation applied to the patch 102.

The microporation occurs with a stainless steel filament 200 having applied thereto an energy pulse of 6.3 mJ per filament to create about 200 pathways with a treated area between about 5% per square centimeter of skin. The patch 102 used for the administration of the peptide shown in graph 1600 has a thickness of 38 μm, a weight of 12 g/m², a WHC of 4 mg/cm², an API of 0.2 mg/cm², and a total solid weight of about 10.2 mg/cm².

The graph 1600 shows the mean profile for the peptide (for example, Lixisenatide) described above when combined with 2.0 mg sucrose and 8.0 mg urea to form the total solid weight of about 10.2 mg/cm². The graph 1600 includes the concentration of the peptide in ng/mL along the y-axis and time in hours (hr) along the x-axis. The graph 1600 shows one line 1602. The line 1602 represents the patch 102 and microporation parameters described above. The line 1602 shows a trend of increasing to a peak concentration value and then decreasing in concentration value.

Based on the graph 1600, the AUC, bioavailability, and maximum concentration value of line 1602 is shown below in Table 14. The AUC is 264.1 ng/mL*hr, the bioavailability is 46.8%, and the maximum concentration is 27.1 ng/mL.

TABLE 14

| Group | AUC (ng/ml*hr) | BA | Cmax |
|---|---|---|---|
| 4 | 264.1 | 46.8 | 27.1 |

Figure 17:
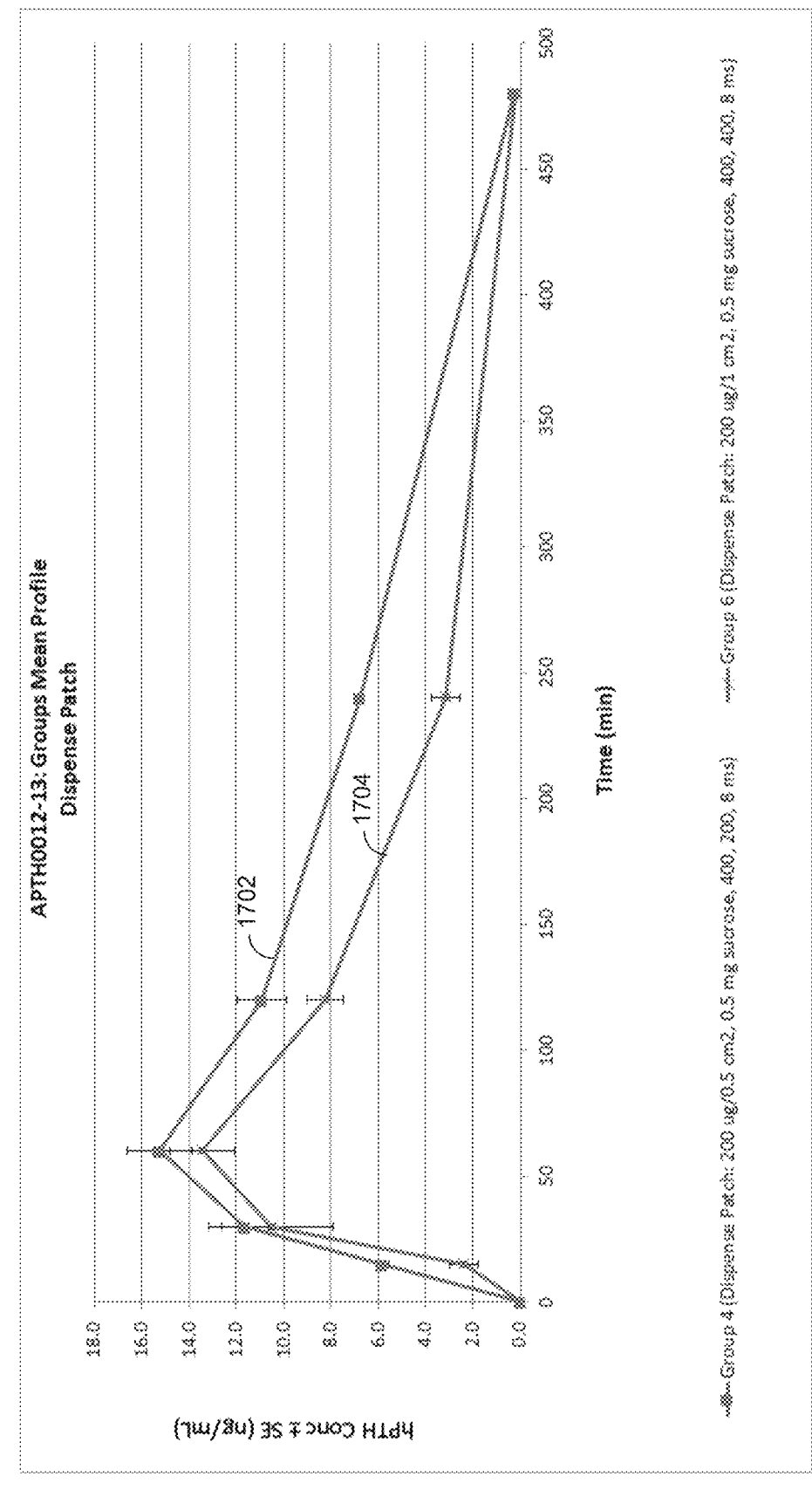
FIG. 17 shows a graph showing blood concentration levels in hairless Guinea pigs when a peptide (for example, Teriparatide) is the type of drug formulation applied to the patch 102.

The graph 1700 in FIG. 17 shows concentration levels in hairless Guinea pigs when a peptide (for example, Teriparatide) is the type of drug formulation applied to the patch 102.

The microporation occurs based on parameters provided in Table 15 below.

TABLE 15

| Group | Energy (mJ/filament) | Filament | Pores | Area | Treated Area |
|---|---|---|---|---|---|
| 4 | 9.3 | Stainless | 200 | 0.5 cm$^2$ | 10%/cm$^2$ |
| 6 | 9.3 | Stainless | 400 | 1.0 cm$^2$ | 10%/cm$^2$ |

Table 15 identifies two groups (group 4 and group 6) that both use stainless steel filaments 200 and create 200 and 400 pathways, respectively, having applied an energy pulse of 9.3 mJ per filament with a treated area of about 10% per square centimeter of skin for 0.5 cm2 and 1.0 cm$^2$, respectively. The patch 102 used for the administration of the peptide shown in graph 1700 has a thickness of 38 μm, a weight of 12 g/m$^2$, a WHC of 4 mg/cm$^2$, an API of 0.2 mg/cm$^2$, and a total solid weight of about 0.7 mg/cm$^2$.

The graph 1700 shows the mean profile for the peptide (for example, hPTH) described above when combined with 0.5 mg sucrose to form the total solid weight of about 0.7 mg/cm$^2$. The graph 1700 includes the concentration of the peptide in ng/mL along the y-axis and time in hours (hr)

ng/mL*hr, the bioavailability is 37.427%, and the maximum concentration is 9.156 ng/mL. For group 6, the AUC is 2208.956 ng/mL*hr, the bioavailability is 25.350%, and the maximum concentration is 11.236 ng/mL.

TABLE 16

| Group | AUC (ng/ml*hr) | BA | Cmax |
|---|---|---|---|
| 4 | 3261.325 | 37.427 | 9.156 |
| 6 | 2208.956 | 25.350 | 11.236 |

Figure 18:
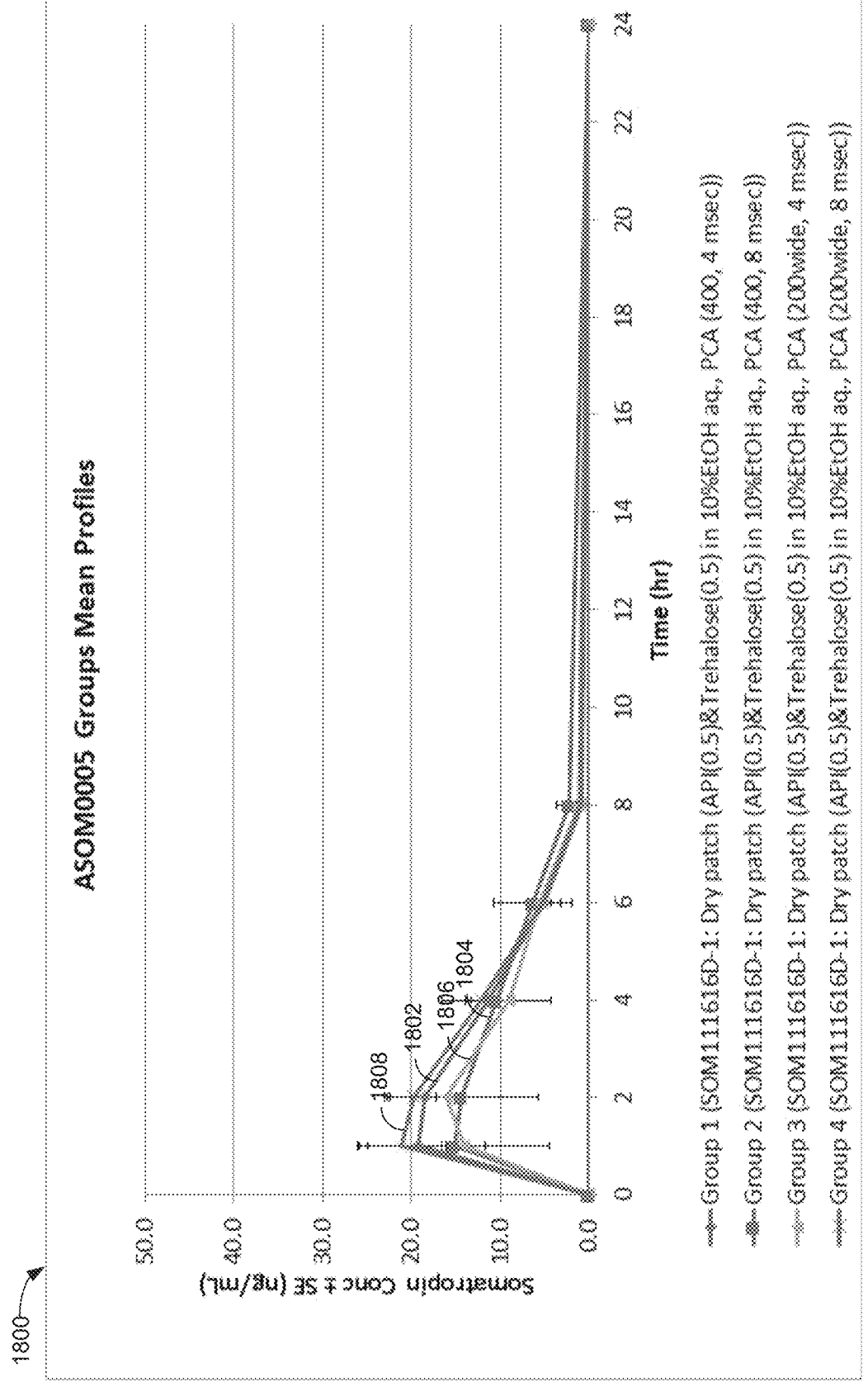
FIG. 18 shows a graph showing a blood comparison of the concentration levels in hairless Guinea pigs when a peptide (for example, Somatropin) is the type of drug formulation applied to the patch 102.

The graph 1800 in FIG. 18 shows a comparison of the blood concentration levels in hairless Guinea pigs when a peptide (for example, Somatropin) is the type of drug formulation applied to the patch 102. The microporation occurs according to the parameters in Table 17. Table 17 shows four groups, each indicating a stainless steel filament 200 having applied thereto an energy pulse of 5.2 mJ and 9.3 mJ per filament to create between about 200 and 400 pathways with a treated area of about 10% per square centimeter of skin. 200 Wide filaments are double the width of standard one (2×50 micrometers) so the energy pulse of 5.2 mJ and 9.3 mJ per filament, thus providing the same current density/flux, and similar power used.

TABLE 17

| Group | Energy (mJ/filament) | Filament | Pores | Area | Treated Area |
|---|---|---|---|---|---|
| 1 | 5.7 | Stainless | 400 | 1.0 cm$^2$ | 10%/cm$^2$ |
| 2 | 9.3 | Stainless | 400 | 1.0 cm$^2$ | 10%/cm$^2$ |
| 3 | 5.2 | Stainless | 200 wide | 1.0 cm$^2$ | 10%/cm$^2$ |
| 4 | 9.3 | Stainless | 200 wide | 1.0 cm$^2$ | 10%/cm$^2$ |

The parameters for the patch 102 used for the four groups are provided in Table 18 below. Table 18 indicates that the patches 102 for each of the groups 1-4 of Table 17 and shown in graph 1800 has a thickness of 38 μm, a weight of 12 g/m$^2$, a WHC of 4 mg/cm$^2$, a drug of 1.0 mg/cm$^2$, and a total solid weight of 1.0 mg/cm$^2$ with an area of 1.0 cm$^2$.

TABLE 18

| Group | Matrix | Thickness (μm) | Weight (g/m$^2$) | WHC (mg/cm$^2$) | Drug | Total Solid | Area |
|---|---|---|---|---|---|---|---|
| 1 | Nonwoven | 38 | 12 | 4 | 0.5 mg (0.5 mg/cm$^2$) | 1.0 mg (1.0 mg/cm$^2$) | 1.0 cm$^2$ |
| 2 | Nonwoven | 38 | 12 | 4 | 0.5 mg (0.5 mg/cm$^2$) | 1.0 mg (1.0 mg/cm$^2$) | 1.0 cm$^2$ |
| 3 | Nonwoven | 38 | 12 | 4 | 0.5 mg (0.5 mg/cm$^2$) | 1.0 mg (1.0 mg/cm$^2$) | 1.0 cm$^2$ |
| 4 | Nonwoven | 38 | 12 | 4 | 0.5 mg (0.5 mg/cm$^2$) | 1.0 mg (1.0 mg/cm$^2$) | 1.0 cm$^2$ | along the x-axis. The graph 1700 shows two lines 1702 and 1704. The line 1702 represents the patch 102 and microporation parameters of group 4 described above. The line 1704 represents the patch 102 and microporation parameters of group 6 described above. Both lines 1702 and 1704 show a general trend of increasing to a peak concentration value and then decreasing in concentration value, where the line 1702 for group 4 shows a greater concentration than the line 1704 for all shown times.

Based on the graph 1700, the AUC, bioavailability, and maximum concentration value of lines 1702 and 1704 are shown below in Table 16. For group 4, the AUC is 3261.325

The graph 1800 shows the mean profile for the peptide (for example, Somatropin) described above for either 200 or 400 pathways and either 4 ms or 8 ms pulses. The graph 1800 includes the concentration of the peptide in ng/mL along the y-axis and time in hours (hr) along the x-axis. The graph 1800 shows four lines 1802, 1804, 1806, and 1808. The line 1802 represents the group 1 parameters from Tables 17 and 18. The line 1804 represents the group 2 parameters from Tables 17 and 18. The line 1806 represents the group 3 parameters from Tables 17 and 18. The line 1808 represents the group 4 parameters from Tables 17 and 18. Each of the four lines 1802, 1804, 1806, and 1808 follow the same general trend of increasing to a peak concentration value and then gradually decreasing in concentration. The line 1808 generally has the highest concentration values, followed by line 1802, then line 1804, and finally line 1806. It is noted that the line 1804 exceeds line 1806 from between about 2 hours to about 3 hours.

Based on the graph 1800, the AUC, the bioavailability, the maximum concentration, and the time at which the maximum concentration occurs are shown below in Table 19. Table 19 shows that each of these values varies for each of the groups. The administration of group 1 results in an AUC of 87.1 ng/mL*hr, a bioavailability of 35.8%, a maximum concentration of 20.4 ng/mL, the maximum concentration occurring 1.3 hr after administration of the drug (after the patch 102 is applied to the skin). The administration of group 2 results in an AUC of 90.1 ng/mL*hr, a bioavailability of 37.0%, and a maximum concentration of 16.1 ng/mL, the maximum concentration occurring 1.8 hr after administration of the drug. The administration of group 3 results in an administration of the vaccine. Table 21 provides parameters for the patch 102 for each of the groups 1-5.

TABLE 20

| Group | Energy (mJ/filament) | Filament | Pores | Area | Treated Area |
|---|---|---|---|---|---|
| 1 | 5.0 | Stainless | 200 | 1.0 cm$^2$ | 5%/cm$^2$ |
| 2 | 5.0 | Stainless | 100 | 0.5 cm$^2$ | 5%/cm$^2$ |
| 3 | 5,0 | Stainless | 50 | 0.25 cm$^2$ | 5%/cm$^2$ |
| 4 | 5.0 | Stainless | 200 | 0.5 cm$^2$ | 10%/cm$^2$ |
| 5 | 3.0 | Stainless | 100 | 0.5 cm$^2$ | 5%/cm$^2$ |
| 6 | Intradermal | — | — | — | — |
| 7 | Intramuscular | — | — | — | — |

TABLE 21

| Group | Matrix | Thickness (μm) | Weight (g/m$^2$) | WHC (mg/cm$^2$) | OVA | Total Solid | Area |
|---|---|---|---|---|---|---|---|
| 1 | Nonwoven | 38 | 12 | 4 | 0.01 mg (0.01 mg/cm$^2$) | 1.01 mg (1.01 mg/cm$^2$) | 1.0 cm$^2$ |
| 2 | Nonwoven | 38 | 12 | 4 | 0.01 mg (0.02 mg/cm$^2$) | 1.01 mg (2.02 mg/cm$^2$) | 0.5 cm$^2$ |
| 3 | Nonwoven | 38 | 12 | 4 | 0.01 mg (0.04 mg/cm$^2$) | 1.01 mg (4.04 mg/cm$^2$) | 0.25 cm$^2$ |
| 4 | Nonwoven | 38 | 12 | 4 | 0.01 mg (0.02 mg/cm$^2$) | 1.01 mg (2.02 mg/cm$^2$) | 0.5 cm$^2$ |
| 5 | Nonwoven | 38 | 12 | 4 | 0.01 mg (0.02 mg/cm$^2$) | 1.01 mg (2.02 mg/cm$^2$) | 0.5 cm$^2$ |

AUC of 78.1 ng/mL*hr, a bioavailability of 32.1%, and a maximum concentration of 16.4 ng/mL, the maximum concentration occurring 1.5 hr after administration of the drug. The administration of group 4 results in an AUC of 94.9 ng/mL*hr, a bioavailability of 32.1%, and a maximum concentration of 16.4 ng/mL, the maximum concentration occurring 1.5 hr after administration of the drug. Thus, the graph 1800 shows the impact the number of power and pulse length has on the delivery of peptides.

TABLE 19

| Group | AUC (ng/ml*hr) | BA | Cmax (ng/mL) | Tmax (hr) |
|---|---|---|---|---|
| 1 | 87.1 | 35.8 | 20.4 | 1.3 |
| 2 | 90.1 | 37.0 | 16.1 | 1.8 |
| 3 | 78.1 | 32.1 | 16.4 | 1.5 |
| 4 | 94.9 | 39.0 | 22.6 | 1.5 |

Figure 19:
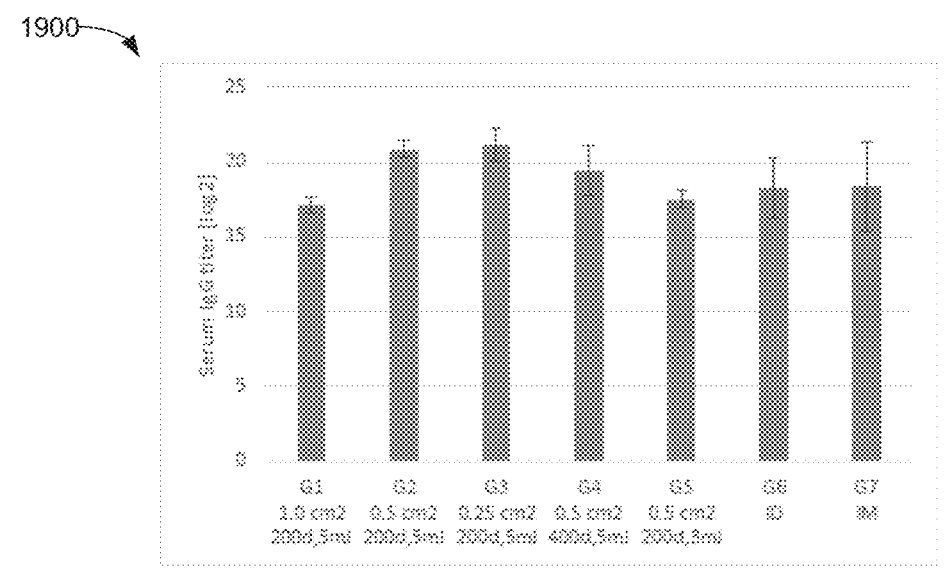
FIG. 19 shows a bar graph 1900 indicating a serum titer amount for seven groups of vaccine administered in rats according to the parameters in Table 20.
Figure 19:
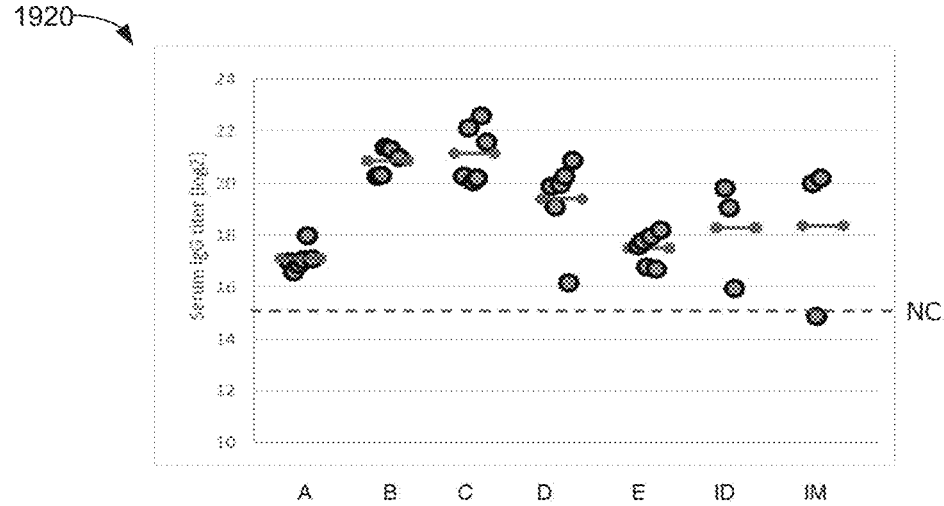

FIG. 19 shows a bar graph 1900 indicating a serum titer amount for seven groups of vaccine administered in rats according to the parameters in Table 20.

Figure 20:
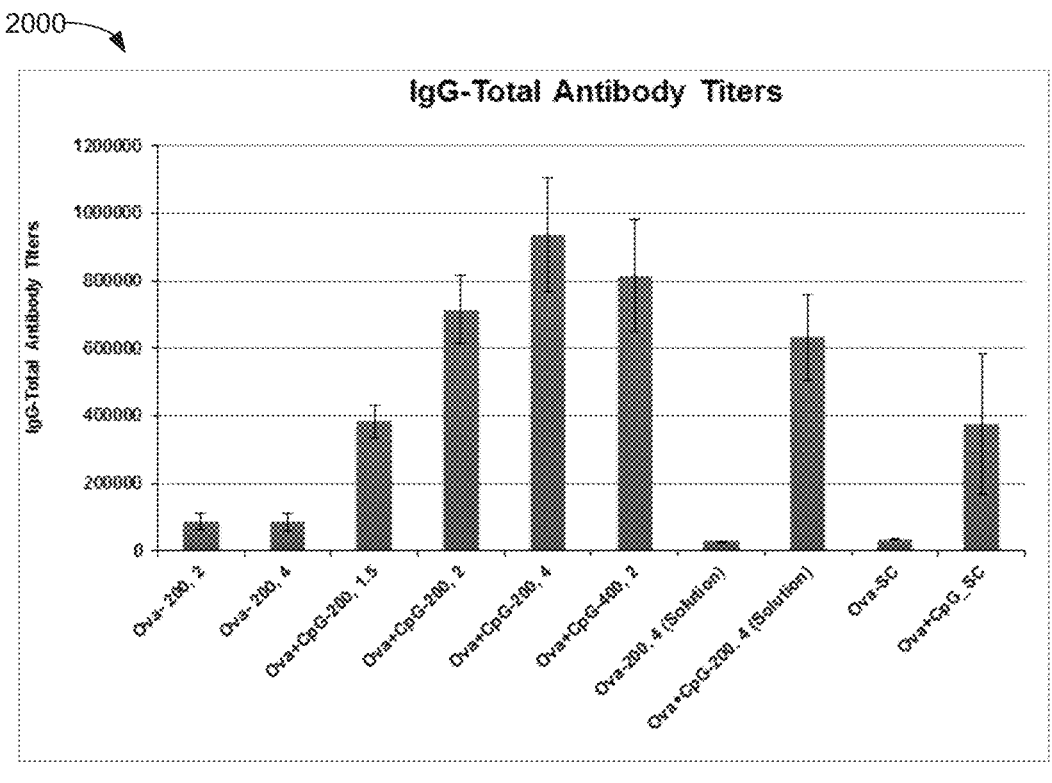
FIG. 20 shows a bar graph 2000 indicating a total amount of antibody titers in mice for groups 1-10 of vaccines
Figure 20:
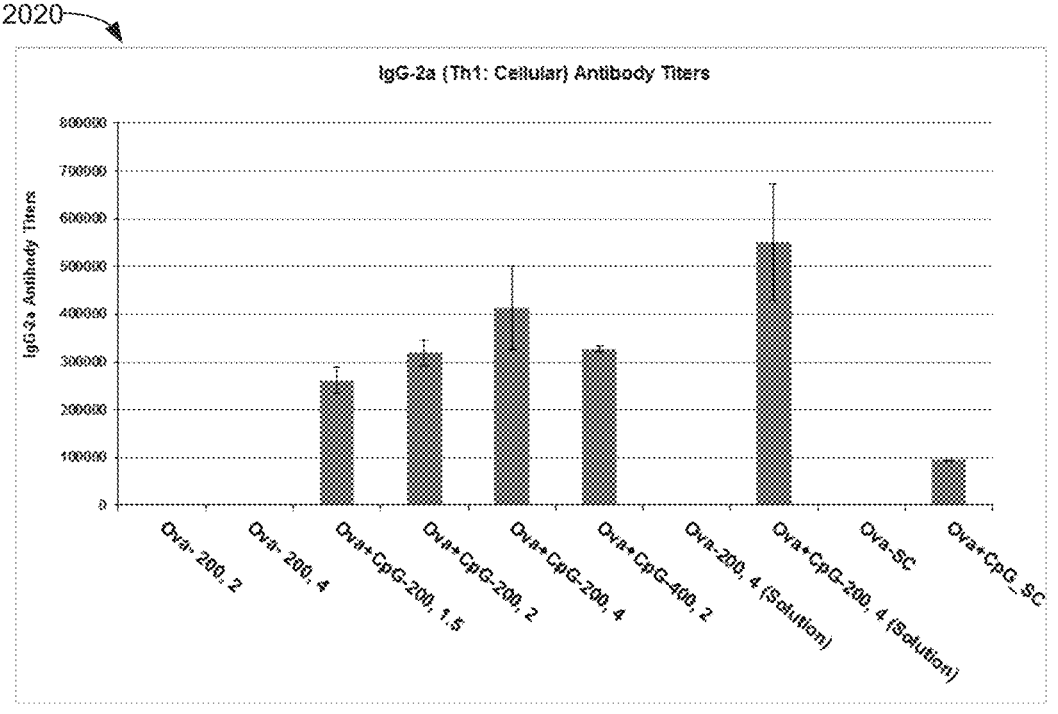

According to Table 20 below, groups 1-5 are vaccine (for example, antigen Ovalbumin) administered using the microporation drug delivery system with different microporation parameters. Group 6 corresponds to an intradermal administration and group 7 corresponds to an intramuscular FIG. 20 shows a bar graph 2000 indicating a total amount of antibody titers in mice for groups 1-10 of vaccines administered according to the parameters in Table 22 and a bar graph 2020 indicating Th1 cellular antibody titers in the body for groups 1-10. According to Table 22 below, groups 1-8 are vaccine (for example, the antigen Ovalbumin with CpG or without adjuvant) administered using the microporation drug delivery system with different microporation parameters. Groups 9 and 10 correspond to intradermal administrations of the vaccine. Table 23 provides parameters for the patch 102 for each of the groups 1-8 and solution values for the groups 9 and 10. Table 24 variables for the dosing provided by the groups 1-10 of Tables 22 and 23.

TABLE 22

| Group | Energy (mJ/filament) | Filament | Pores | Area | Treated Area |
|---|---|---|---|---|---|
| 1 | 3.3 | Stainless | 200 | 1.0 cm$^2$ | 5%/cm$^2$ |
| 2 | 6.4 | Stainless | 200 | 1.0 cm$^2$ | 5%/cm$^2$ |
| 3 | 3.3 | Stainless | 200 | 1.0 cm$^2$ | 5%/cm$^2$ |
| 4 | 6.4 | Stainless | 200 | 1,0 cm$^2$ | 5%/cm$^2$ |
| 5 | 2.5 | Stainless | 200 | 1.0 cm$^2$ | 5%/cm$^2$ |
| 6 | 2.5 | Stainless | 400 | 1.0 cm$^2$ | 10%/cm$^2$ |
| 7 | 6.4 | Stainless | 200 | 1,0 cm$^2$ | 5%/cm$^2$ |
| 8 | 6.4 | Stainless | 200 | 1.0 cm$^2$ | 5%/cm$^2$ |
| 9 | ID | — | — | — | — |
| 10 | ID | — | — | — | — |

TABLE 23

| Group | Matrix | Thickness (μm) | Weight (g/m$^2$) | WHC (mg/cm$^2$) | OVA + CpG | Total Solid | Area |
|---|---|---|---|---|---|---|---|
| 1 | Nonwoven | 38 | 12 | 4 | 0.1 mg (0.1 mg/cm$^2$) | 2.1 mg (2.1 mg/cm$^2$) | 1.0 cm$^2$ |
| 2 | Nonwoven | 38 | 12 | 4 | 0.1 mg (0.1 mg/cm$^2$) | 2.1 mg (2.1 mg/cm$^2$) | 1.0 cm$^2$ |
| 3 | Nonwoven | 38 | 12 | 4 | 0.1 mg + 0.02 mg (0.12 mg/cm$^2$) | 2.12 mg (2.12 mg/cm$^2$) | 1.0 cm$^2$ |

TABLE 23-continued

| Group | Matrix | Thickness (μm) | Weight (g/m²) | WHC (mg/cm²) | OVA + CpG | Total Solid | Area |
|---|---|---|---|---|---|---|---|
| 4 | Nonwoven | 38 | 12 | 4 | 0.1 mg + 0.02 mg (0.12 mg/cm²) | 2.12 mg (2.12 mg/cm²) | 1.0 cm² |
| 5 | Nonwoven | 38 | 12 | 4 | 0.1 mg + 0.02 mg (0.12 mg/cm²) | 2.12 mg (2.12 mg/cm²) | 1.0 cm² |
| 6 | Nonwoven | 38 | 12 | 4 | 0.1 mg + 0.02 mg (0.12 mg/cm²) | 2.12 mg (2.12 mg/cm²) | 1.0 cm² |
| 7 | Nonwoven | 38 | 12 | 4 | 0.1 mg (0.12 mg/cm²) | 2.1 mg solution | 1.0 cm² |
| 8 | Nonwoven | 38 | 12 | 4 | 0.1 mg + 0.02 mg (0.12 mg/cm²) | 2.12 mg solution | 1.0 cm² |
| 9 | ID | — | — | — | 0.1 mg | 2.1 mg solution | — |
| 10 | ID | — | — | — | 0.1 mg + 0.02 mg | 2.12 mg solution | — |

TABLE 24

| Group | Dose (mg) | CpG (mg) | Sucrose (mg) | Pore Density (#) | Energy Pulse (ms) |
|---|---|---|---|---|---|
| 1 | 0.1 | N/A | 2 | 200 | 2 |
| 2 | 0.1 | N/A | 2 | 200 | 4 |
| 3 | 0.1 | 0.02 | 2 | 200 | 1.5 |
| 4 | 0.1 | 0.02 | 2 | 200 | 2 |
| 5 | 0.1 | 0.02 | 2 | 400 | 4 |
| 6 | 0.1 | 0.02 | 2 | 200 | 2 |
| 7 | 0.1 | N/A | 2 | 200 | 4 |
| 8 | 0.1 | 0.02 | 2 | 200 | 4 |
| 9 | 0.1 | N/A | 2 | N/A | N/A |
| 10 | 0.1 | 0.02 | 2 | N/A | N/A |

FIG. 21 shows a bar graph 2100 indicating a total amount of antibody titers in mice for groups 1-6 of vaccines administered according to the parameters in Table 22 and a bar graph 2120 indicating Th1 humoral antibody titers in the body for groups 1-6. According to Table 25 below, groups 1-5 are vaccine (for example, the antigen Ovalbumin without adjuvant) administered using the microporation drug delivery system with different microporation parameters. Group 6 corresponds to intradermal administrations of the vaccine. Table 26 provides parameters for the patch 102 for each of the groups 1-5 and solution values for the group 6. Table 27 variables for the dosing provided by the groups 1-6 of Tables 26 and 27. Immunoresponse is illustrated under several conditions: CpG (adjuvant), sucrose content, applicator conditions, and different holding materials.

Those of skill will recognize that the various illustrative logical blocks, modules, circuits, and algorithm steps described as follows, and in connection with the embodiments disclosed herein may be implemented as electronic hardware, software stored on a computer readable medium and executable by a hardware processor, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor reads information from, and write information to, the storage medium. In the alternative, the storage medium may be integral to the processor. The processor and the storage medium may reside in an ASIC.

While the above detailed description has shown, described, and pointed out novel features of the development as applied to various embodiments, it will be understood that various omissions, substitutions, and changes in the form and details of the device or process illustrated may be made by those skilled in the art without departing from the spirit of the development. As will be recognized, the present development may be embodied within a form that does not provide all of the features and benefits set forth herein, as some features may be used or practiced separately from others. All changes which come within the meaning and range of equivalency of the claims are to be embraced within their scope.

A person skilled in the art will recognize that each of these sub-systems may be inter-connected and controllably connected using a variety of techniques and hardware and that the present disclosure is not limited to any specific method of connection or connection hardware.

The technology is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, a microcontroller or microcontroller based system, programmable consumer electronics, network PCs, minicomputers, mainframe computers, distributed computing environments that include any of the above systems or devices, and the like.

As used herein, instructions refer to computer-implemented steps for processing information in the system. Instructions may be implemented in software, firmware or hardware and include any type of programmed step undertaken by components of the system.

A microprocessor may be any conventional general purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special purpose microprocessor such as a digital signal processor or a graphics processor. The microprocessor typically has conventional address lines, conventional data lines, and one or more conventional control lines.

The system may be used in connection with various operating systems such as Linux®, UNIX®, MacOS® or Microsoft Windows®, or custom made one.

The system control may be written in any conventional programming language such as C, C++, BASIC, Pascal, .NET (e.g., C#), or Java, and ran under a conventional operating system. C, C++, BASIC, Pascal. Java, and FORTRAN are industry standard programming languages for which many commercial compilers may be used to create executable code. The system control may also be written using interpreted languages such as Perl, Python or Ruby. Other languages may also be used such as PHP, JavaScript, and the like.

The foregoing description details certain embodiments of the systems, devices, and methods disclosed herein. It will be appreciated, however, that no matter how detailed the foregoing appears in text, the systems, devices, and methods may be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment may be included with other depicted embodiments in any combination. For example, any of the various components described herein and/or depicted in the Figures may be combined, interchanged or excluded from other embodiments.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present development. This development is susceptible to modifications in the methods and materials, as well as alterations in the fabrication methods and equipment. Such modifications will become apparent to those skilled in the art from a consideration of this disclosure or practice of the development disclosed herein. Consequently, it is not intended that this development be limited to the specific embodiments disclosed herein, but that it cover all modifications and alternatives coming within the true scope and spirit of the development as embodied in the attached claims.

As will be understood by those of skill in the art, in some embodiments, the processes set forth in the following material may be performed on a computer network. The computer network having a central server, the central server having a processor, data storage, such as databases and memories, and communications features to allow wired or wireless communication with various parts of the networks, including terminals and any other desired network access point or means.

What is claimed is:

1. A transdermal permeant delivery system for delivery of at least one permeant into a tissue membrane of a subject, comprising:
   a) a substrate having an upper substrate surface and defining a poration area, the substrate comprising a filament array having a plurality of filaments that are disposed in the poration area, wherein each filament is capable of conductively delivering thermal energy via direct contact to the tissue membrane to form a plurality of micropores in a micropore area of the tissue membrane that is in the range of 1% to 20% of the poration area;
   b) an applicator electrically connected to the filament array and configured to supply a controlled amount of electrical energy to the filaments in order to create the plurality of micropores in the micropore area of the tissue membrane by heating the filaments; and
   c) a patch configured for application on the micropore area and for releasably containing the at least one permeant, the patch comprising a matrix having a water-holding capacity that is less than 10 mg cm$^2$ and the at least one permeant dispersed in the matrix, wherein the water-holding capacity is the maximum amount of moisture the matrix can hold per unit area (cm$^2$) of the matrix.

2. The system of claim 1, wherein the system is configured to deliver controlled electrical energy to create the plurality of micropores by heating the filaments in the range of 0.0067 µJ/µm$^3$ to 0.0400 µJ/µm$^3$ measured in microjoules per unit volume (µm$^3$) of the plurality of filaments.

3. The system of claim 1, wherein the micropore area is in the range of 1.25% to 10% of the poration area.

4. The system of claim 1, wherein the system is configured to form a plurality of micropores such that the accumulated volume of the plurality of micropores is in the range of 0.05 mm$^3$/cm$^2$ to 0.35 mm$^3$/cm$^2$ measured in cubic millimeters of the plurality of micropores per unit area (cm$^2$) of the poration area.

5. The system of claim 1, wherein the at least one permeant is a long acting drug.

6. The system of claim 5, wherein the long acting drug is a GLP-1 antagonist, a Fc protein, an antibody or a derivative thereof having an extended half-life.

7. The system of claim 5, wherein the patch is configured to release the long acting drug for more than 24 hours.

8. The system of claim 5, wherein the patch is configured to release the long acting drug for between 1 and 7 days.

9. The system of claim 5, wherein the patch is configured to release the long acting drug for more than 7 days.

10. The system of claim 1, further comprising a backing layer having at least a partial adhesive.

11. The system of claim 1, wherein the plurality of filaments comprise a conductive layer of copper and an underlying resistive layer of stainless steel.

12. The system of claim 1, wherein the applicator is configured to supply the controlled electrical energy to the filaments in the range of 2 mJ/filament to 12 mJ/filament.

13. The system of claim 1, wherein the applicator is configured to supply the controlled electrical energy to the filaments for a time in the range of 2 ms to 12 ms.

14. The system of claim 1, wherein the system is configured to form a plurality of micropores such that the plurality of micropores in the micropore area are present at about 50 micropores/cm$^2$ to about 400 micropores/cm$^2$ measured in the number of micropores per unit area (cm$^2$) of the poration area.

15. The system of claim 1, wherein the system is configured to form a plurality of micropores such that the accumulated depth of the plurality of micropores is in the range of about 2500 μm/cm$^2$ to about 30,000 μm/cm$^2$ measured in the accumulated depth of the plurality of micropores per unit area (cm$^2$) of the poration area.

16. The system of claim 1, wherein the matrix comprises at least one fiber.

17. The system of claim 16, wherein the matrix comprises a laminated material, the laminated material comprising the at least one fiber and a film.

18. The system of claim 16, wherein the at least one fiber has a thickness of less than 300 μm.

19. The system of claim 16, wherein the areal weight of the at least one fiber in the matrix is less than about 100 g/m$^2$ measured in grams of the at least one fiber per unit area (m$^2$) of the at least one fiber.

20. The system of claim 16, wherein the at least one fiber is a nonwoven fiber.

21. The system of claim 1, wherein the at least one permeant is dispersed in the matrix in an amount in the range of about 0.01 mg/cm$^2$ to about 20 mg/cm$^2$ measured in milligrams of the at least one permeant per unit area (cm$^2$) of the matrix.

22. The system of claim 1, wherein the at least one permeant is a small molecule, a peptide, a protein, an oligonucleotide or a combination thereof.

23. The system of claim 1, wherein the water-holding capacity of the matrix is in the range of 1 mg/cm$^2$ to 10 mg/cm$^2$.

24. A method of treating a subject in need thereof, comprising:

identifying a subject having a condition in need of treatment by a selected drug;

opening a plurality of micropores in the tissue membrane of the subject by applying the applicator of the transdermal permeant delivery system of claim 1, to the subject; and applying the patch of the transdermal permeant delivery system of claim 1 to the subject's skin over the plurality of micropores for a period of time, wherein the at least one permeant dispersed in the matrix of the patch comprises the selected drug;

wherein the period of time is selected to deliver a therapeutically effective amount of the selected drug through the plurality of micropores.

25. A transdermal permeant delivery system for delivery of at least one permeant into a tissue membrane of a subject, comprising:

a) a substrate having an upper substrate surface and defining a poration area, the substrate comprising a filament array having a plurality of filaments that are disposed in the poration area, wherein each filament is capable of conductively delivering thermal energy via direct contact to the tissue membrane to form a plurality of micropores in a micropore area of the tissue membrane; and b) an applicator electrically connected to the filament array and configured to supply a controlled electrical energy to the filaments in order to create the plurality of micropores in the micropore area of the tissue membrane by heating the filaments;

wherein the system is configured to deliver controlled electrical energy to create the plurality of micropores by heating the filaments in the range of 0.0067 μJ/μm$^3$ to 0.0400 μJ/μm$^3$ measured in microjoules per unit volume (μm$^3$) of the plurality of filaments.

26. The transdermal permeant delivery system of claim 25, further comprising:

c) a patch configured for application on the micropore area and for releaseably containing at least one permeant, the patch comprising a matrix having a water-holding capacity in the range of 1 mg/cm$^2$ to 10 mg cm$^2$ and the at least one permeant dispersed in the matrix, wherein the water-holding capacity is the maximum amount of moisture the matrix can hold per unit area (cm$^2$) of the matrix.

27. The transdermal permeant delivery system of claim 25, wherein the applicator is configured to deliver the controlled electrical energy for a time in the range of 2 ms to 12 ms.

* * * * *